US008282660B2

(12) United States Patent
Thompson et al.

(10) Patent No.: US 8,282,660 B2
(45) Date of Patent: Oct. 9, 2012

(54) MINIMALLY INVASIVE LUNG VOLUME REDUCTION DEVICES, METHODS, AND SYSTEMS

(75) Inventors: David Thompson, San Jose, CA (US); Nathan Aronson, Chico, CA (US); Patrick Wu, Pleasanton, CA (US); David Lehrberg, Mountain View, CA (US); Mark L. Mathis, Fremont, CA (US); Michael Boutillette, San Francisco, CA (US); Jaime Vasquez, Fremont, CA (US)

(73) Assignee: PneumRx, Inc., Mountain View, CA (US)

( * ) Notice: Subject to any disclaimer, the term of this patent is extended or adjusted under 35 U.S.C. 154(b) by 1003 days.

(21) Appl. No.: 12/167,167

(22) Filed: Jul. 2, 2008

(65) Prior Publication Data

US 2009/0012626 A1    Jan. 8, 2009

Related U.S. Application Data

(63) Continuation of application No. PCT/US2007/006339, filed on Mar. 13, 2007, which is a continuation-in-part of application No. 11/422,047, filed on Jun. 2, 2006, now Pat. No. 8,157,537.

(60) Provisional application No. 60/743,471, filed on Mar. 13, 2006, provisional application No. 60/884,804, filed on Jan. 12, 2007, provisional application No. 60/885,305, filed on Jan. 17, 2007.

(51) Int. Cl.
*A61B 17/08* (2006.01)

(52) U.S. Cl. ..................... 606/157; 623/23.65

(58) Field of Classification Search ............... 623/23.65, 623/23.64; 606/151, 157
See application file for complete search history.

(56) References Cited

U.S. PATENT DOCUMENTS

| | | |
|---|---|---|
| 3,559,652 A | 2/1971 | Banitt et al. |
| 4,013,080 A | 3/1977 | Froning |
| 4,153,058 A | 5/1979 | Nehme |
| 4,233,984 A | 11/1980 | Walling |
| 4,245,624 A | 1/1981 | Komiya |
| 4,479,792 A | 10/1984 | Lazarus et al. |
| 4,494,531 A | 1/1985 | Gianturco |

(Continued)

FOREIGN PATENT DOCUMENTS

FR          28407961          12/2003

(Continued)

OTHER PUBLICATIONS

International Search Report and Written Opinion of PCT Application No. PCT/US2009/056839, mailed on Jan. 4, 2010, 15 pages total.

(Continued)

*Primary Examiner* — Corrine M McDermott
*Assistant Examiner* — Gregory Anderson
(74) *Attorney, Agent, or Firm* — Kilpatrick Townsend & Stockton LLP

(57) ABSTRACT

A lung volume reduction system is disclosed comprising an implantable device adapted to be delivered to a lung airway of a patient in a delivery configuration and to change to a deployed configuration to bend the lung airway. The invention also discloses a method of bending a lung airway of a patient comprising inserting a device into the airway in a delivery configuration and bending the device into a deployed configuration, thereby bending the airway.

38 Claims, 39 Drawing Sheets

U.S. PATENT DOCUMENTS

| | | |
|---|---|---|
| 4,532,935 A | 8/1985 | Wang |
| 4,702,260 A | 10/1987 | Wang |
| 4,739,760 A | 4/1988 | Chin et al. |
| 4,766,906 A | 8/1988 | Wang |
| 4,769,017 A | 9/1988 | Fath et al. |
| 4,821,722 A | 4/1989 | Miller et al. |
| 4,880,015 A | 11/1989 | Nierman |
| 5,056,529 A | 10/1991 | de Groot |
| 5,084,012 A | 1/1992 | Kelman |
| 5,108,368 A | 4/1992 | Hammerslag et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman |
| 5,240,011 A | 8/1993 | Assa |
| 5,261,889 A | 11/1993 | Laine et al. |
| 5,312,329 A | 5/1994 | Beaty et al. |
| 5,312,331 A | 5/1994 | Knoepfler |
| 5,315,992 A | 5/1994 | Dalton |
| 5,334,183 A | 8/1994 | Wuchinich |
| 5,354,287 A | 10/1994 | Wacks |
| 5,385,606 A | 1/1995 | Kowanko |
| 5,423,830 A | 6/1995 | Schneebaum et al. |
| 5,484,401 A | 1/1996 | Rodriguez et al. |
| 5,514,536 A | 5/1996 | Taylor |
| 5,522,819 A | 6/1996 | Graves et al. |
| 5,526,821 A | 6/1996 | Jamshidi |
| 5,549,551 A * | 8/1996 | Peacock et al. .......... 604/103.05 |
| 5,549,904 A | 8/1996 | Juergensen et al. |
| 5,599,294 A | 2/1997 | Edwards et al. |
| 5,660,175 A | 8/1997 | Dayal |
| 5,660,185 A | 8/1997 | Shmulewitz et al. |
| 5,697,365 A | 12/1997 | Pel |
| 5,735,264 A | 4/1998 | Siczek et al. |
| 5,736,132 A | 4/1998 | Juergensen et al. |
| 5,750,657 A | 5/1998 | Edwardson et al. |
| 5,762,070 A | 6/1998 | Nagamatsu |
| 5,846,235 A | 12/1998 | Pasricha et al. |
| 5,875,692 A | 3/1999 | Lin |
| 5,895,417 A | 4/1999 | Pomeranz et al. |
| 5,916,210 A | 6/1999 | Winston |
| 5,916,212 A | 6/1999 | Baust et al. |
| 5,938,635 A | 8/1999 | Kuhle |
| 5,954,636 A | 9/1999 | Schwartz et al. |
| 5,957,919 A | 9/1999 | Laufer |
| 5,964,770 A | 10/1999 | Flomenblit et al. |
| 5,972,026 A | 10/1999 | Laufer et al. |
| 5,978,697 A | 11/1999 | Maytal et al. |
| 6,066,090 A | 5/2000 | Yoon |
| 6,080,113 A | 6/2000 | Heneveld et al. |
| 6,083,255 A | 7/2000 | Laufer et al. |
| 6,123,665 A | 9/2000 | Kawano |
| 6,174,323 B1 | 1/2001 | Biggs et al. |
| 6,183,498 B1 | 2/2001 | DeVore et al. |
| 6,196,966 B1 | 3/2001 | Kerin et al. |
| 6,200,333 B1 | 3/2001 | Laufer |
| 6,245,090 B1 | 6/2001 | Gilson et al. |
| 6,258,100 B1 | 7/2001 | Alferness et al. |
| 6,267,732 B1 | 7/2001 | Heneveld et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,287,304 B1 | 9/2001 | Eggers et al. |
| 6,293,951 B1 | 9/2001 | Alferness et al. |
| 6,299,633 B1 | 10/2001 | Laufer |
| 6,306,141 B1 | 10/2001 | Jervis |
| 6,310,166 B1 | 10/2001 | Hickey et al. |
| 6,312,428 B1 | 11/2001 | Eggers et al. |
| 6,315,737 B1 | 11/2001 | Skinner |
| 6,328,689 B1 | 12/2001 | Gonzalez et al. |
| 6,328,701 B1 | 12/2001 | Terwilliger |
| 6,352,503 B1 | 3/2002 | Matsui et al. |
| 6,379,373 B1 | 4/2002 | Sawhney et al. |
| 6,387,044 B1 | 5/2002 | Tachibana et al. |
| 6,390,967 B1 | 5/2002 | Forman et al. |
| 6,398,775 B1 | 6/2002 | Perkins et al. |
| 6,402,701 B1 | 6/2002 | Kaplan et al. |
| 6,402,754 B1 | 6/2002 | Gonzalez |
| 6,402,781 B1 | 6/2002 | Langberg et al. |
| 6,411,852 B1 | 6/2002 | Danek et al. |
| 6,416,554 B1 | 7/2002 | Alferness et al. |
| 6,443,944 B1 | 9/2002 | Doshi et al. |
| 6,447,534 B2 | 9/2002 | Cragg et al. |
| 6,464,648 B1 | 10/2002 | Nakamura |
| 6,474,340 B1 | 11/2002 | Vaska et al. |
| 6,478,730 B1 | 11/2002 | Bala et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,494,844 B1 | 12/2002 | Van Bladel et al. |
| 6,494,897 B2 | 12/2002 | Sterman et al. |
| 6,509,031 B1 | 1/2003 | Miller et al. |
| 6,514,290 B1 | 2/2003 | Loomas |
| 6,514,522 B2 | 2/2003 | Domb |
| 6,527,761 B1 | 3/2003 | Soltesz et al. |
| 6,537,195 B2 | 3/2003 | Forman |
| 6,537,314 B2 | 3/2003 | Langberg et al. |
| 6,540,694 B1 | 4/2003 | Van Bladel et al. |
| 6,540,716 B1 | 4/2003 | Holm |
| 6,549,800 B1 | 4/2003 | Atalar et al. |
| 6,551,255 B2 | 4/2003 | Van Bladel et al. |
| 6,551,302 B1 | 4/2003 | Rosinko et al. |
| 6,552,172 B2 | 4/2003 | Marx et al. |
| 6,558,337 B2 | 5/2003 | Dvorak et al. |
| 6,568,387 B2 | 5/2003 | Davenport et al. |
| 6,569,166 B2 | 5/2003 | Gonzalez |
| 6,577,893 B1 | 6/2003 | Besson et al. |
| 6,585,639 B1 | 7/2003 | Kotmel et al. |
| 6,589,161 B2 | 7/2003 | Corcoran |
| 6,592,559 B1 | 7/2003 | Pakter et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,622,731 B2 | 9/2003 | Daniel et al. |
| 6,629,951 B2 | 10/2003 | Laufer et al. |
| 6,632,222 B1 | 10/2003 | Edwards et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,275 B1 | 10/2003 | McGaffigan et al. |
| 6,652,516 B1 | 11/2003 | Gough |
| 6,652,520 B2 | 11/2003 | Moorman et al. |
| 6,653,525 B2 | 11/2003 | Ingenito et al. |
| 6,663,624 B2 | 12/2003 | Edwards et al. |
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,977 B1 | 2/2004 | Federowicz et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,814,778 B1 | 11/2004 | Farnworth |

| | | |
|---|---|---|
| 6,817,973 B2 | 11/2004 | Merril et al. |
| 6,825,091 B2 | 11/2004 | Bae et al. |
| 6,827,086 B2 | 12/2004 | Shuman |
| 6,827,683 B2 | 12/2004 | Otawara |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,907,881 B2 | 6/2005 | Suki et al. |
| 6,908,440 B2 | 6/2005 | Fisher |
| 6,918,881 B2 | 7/2005 | Miller et al. |
| 6,929,637 B2 | 8/2005 | Gonzalez et al. |
| 6,936,014 B2 | 8/2005 | Vetter et al. |
| 6,941,950 B2 | 9/2005 | Wilson et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 6,979,344 B2 | 12/2005 | Jones et al. |
| 6,986,737 B2 | 1/2006 | Suzuki et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,063,682 B1 | 6/2006 | Whayne et al. |
| 7,100,616 B2 | 9/2006 | Springmeyer |
| 7,112,225 B2 | 9/2006 | Ginn |
| 7,128,747 B2 | 10/2006 | Ginn |
| 7,141,046 B2 | 11/2006 | Perkins et al. |
| 7,165,548 B2 | 1/2007 | Deem et al. |
| 7,175,619 B2 | 2/2007 | Koblish et al. |
| 7,195,017 B2 | 3/2007 | Tanaka |
| 7,300,428 B2 | 11/2007 | Ingenito |
| 7,351,202 B2 | 4/2008 | Long |
| 7,393,330 B2 | 7/2008 | Keast et al. |
| 7,393,363 B2 | 7/2008 | Ginn |
| 7,445,010 B2 | 11/2008 | Kugler et al. |
| 7,451,765 B2 | 11/2008 | Adler |
| 7,503,931 B2 | 3/2009 | Kowalsky et al. |
| 7,517,320 B2 | 4/2009 | Wibowo et al. |
| 7,549,984 B2 | 6/2009 | Mathis |
| 7,608,579 B2 | 10/2009 | Gong et al. |
| 7,662,181 B2 | 2/2010 | Deem et al. |
| 7,731,651 B2 | 6/2010 | Pearce et al. |
| 7,757,691 B2 | 7/2010 | Reynolds et al. |
| 7,766,891 B2 | 8/2010 | McGurk et al. |
| 7,766,895 B2 | 8/2010 | Soltesz et al. |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161392 A1 | 10/2002 | Dubrul |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0192551 A1 | 10/2003 | Deem et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | De Vore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0120849 A1 | 6/2004 | Stewart et al. |
| 2004/0133168 A1 | 7/2004 | Salcudean et al. |
| 2004/0134487 A1 | 7/2004 | Deem et al. |
| 2004/0154621 A1 | 8/2004 | Deem et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0176833 A1 | 9/2004 | Pavenik et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2004/0267277 A1 | 12/2004 | Zannis et al. |
| 2005/0004599 A1 | 1/2005 | McNally-Heintzelman et al. |
| 2005/0015106 A1 | 1/2005 | Perkins et al. |
| 2005/0033344 A1 | 2/2005 | Dillard et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0051163 A1 | 3/2005 | Deem et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0085801 A1 | 4/2005 | Cooper et al. |

| | | |
|---|---|---|
| 2005/0096529 A1 | 5/2005 | Cooper et al. |
| 2005/0101836 A1 | 5/2005 | Onuki et al. |
| 2005/0103340 A1 | 5/2005 | Wondka |
| 2005/0107783 A1 | 5/2005 | Tom et al. |
| 2005/0119614 A1 | 6/2005 | Mesky |
| 2005/0131339 A1 | 6/2005 | Makin et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0148902 A1 | 7/2005 | Minar et al. |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178389 A1 | 8/2005 | Shaw et al. |
| 2005/0192526 A1 | 9/2005 | Biggs et al. |
| 2005/0196344 A1 | 9/2005 | McCutcheon et al. |
| 2005/0244401 A1 | 11/2005 | Ingenito |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004388 A1 | 1/2006 | Whayne et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0020243 A1* | 1/2006 | Speck et al. ............. 604/103.02 |
| 2006/0025815 A1 | 2/2006 | McGurk et al. |
| 2006/0030863 A1 | 2/2006 | Fields et al. |
| 2006/0032497 A1 | 2/2006 | Doshi |
| 2006/0076023 A1 | 4/2006 | Rapacki et al. |
| 2006/0095002 A1 | 5/2006 | Soltesz et al. |
| 2006/0100666 A1 | 5/2006 | Wilkinson et al. |
| 2006/0116749 A1 | 6/2006 | Willink et al. |
| 2006/0118126 A1 | 6/2006 | Tanaka |
| 2006/0124126 A1 | 6/2006 | Tanaka |
| 2006/0135947 A1 | 6/2006 | Soltesz et al. |
| 2006/0135984 A1 | 6/2006 | Kramer et al. |
| 2006/0162731 A1 | 7/2006 | Wondka et al. |
| 2006/0167416 A1 | 7/2006 | Mathis et al. |
| 2006/0200076 A1 | 9/2006 | Gonzalez et al. |
| 2006/0206147 A1 | 9/2006 | DeVore et al. |
| 2006/0235432 A1 | 10/2006 | DeVore et al. |
| 2006/0235467 A1 | 10/2006 | DeVore et al. |
| 2006/0249164 A1 | 11/2006 | Springmeyer |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0096048 A1 | 5/2007 | Clerc |
| 2007/0221230 A1 | 9/2007 | Thompson et al. |
| 2008/0063693 A1 | 3/2008 | Cook |
| 2008/0161865 A1 | 7/2008 | Hagen |
| 2008/0183204 A1 | 7/2008 | Greenhalgh et al. |
| 2009/0076622 A1 | 3/2009 | Thompson et al. |
| 2009/0076623 A1 | 3/2009 | Mathis et al. |
| 2009/0104183 A1 | 4/2009 | Gong et al. |
| 2009/0221967 A1 | 9/2009 | Thommen et al. |
| 2010/0070050 A1 | 3/2010 | Mathis et al. |
| 2010/0100196 A1 | 4/2010 | Thompson et al. |
| 2010/0305715 A1 | 12/2010 | Mathis et al. |

FOREIGN PATENT DOCUMENTS

| | | |
|---|---|---|
| GB | 2324729 | 1/2002 |
| WO | WO 94/01508 A1 | 1/1994 |
| WO | WO 98/01084 A1 | 1/1998 |
| WO | WO 00/13592 | 3/2000 |
| WO | WO 01/13839 | 3/2001 |
| WO | WO 01/54618 A1 | 8/2001 |
| WO | WO 02/00270 | 1/2002 |
| WO | WO 02/00275 | 1/2002 |
| WO | WO 02/02158 | 1/2002 |
| WO | WO 03/077768 | 9/2003 |
| WO | WO 2004/062505 | 7/2004 |
| WO | WO 2004/086977 | 10/2004 |
| WO | WO 2005/122870 | 12/2005 |
| WO | WO 2007/106495 | 9/2007 |
| WO | WO 2008/036763 A2 | 3/2008 |

OTHER PUBLICATIONS

U.S. Appl. No. 60/885,305, filed Jan. 17, 2007; first named inventor: David Thompson.

Supplementary European Search Report of EP Application No. 07752999.8, mailed Sep. 22, 2009, 12 pages total.

Hermanson, Greg T. Bioconjugate Techniques. San Diego: Academic Press, Inc. 1996. (Table of contents only).

International Search Report of PCT Application No. PCT/US07/06339, dated May 14, 2008, 5 pages total.

Lam, et al. X-Ray Diagnosis: A Physician's Approach. Singapore: Springer. 1998. (Table of contents only).

Rowe, et al. Handbook of Pharmaceutical Excipients. 4th Edition. London: Pharmaceutical Press. 2003. (Table of contents only).

Slone, et al. Body CT: A Practical Approach. New York: McGraw-Hill. 2000. (Table of contents only).

Stout, et al. X-Ray Structure Determination: A Practical Guide. 2nd Edition. New York: John Wiley & Sons. 1989. (Table of contents only).

The United States Pharmacopeia. 29th Revision. 2006. The United States Pharmacopeia Convention. Rockville, MD. (Table of contents only).

* cited by examiner

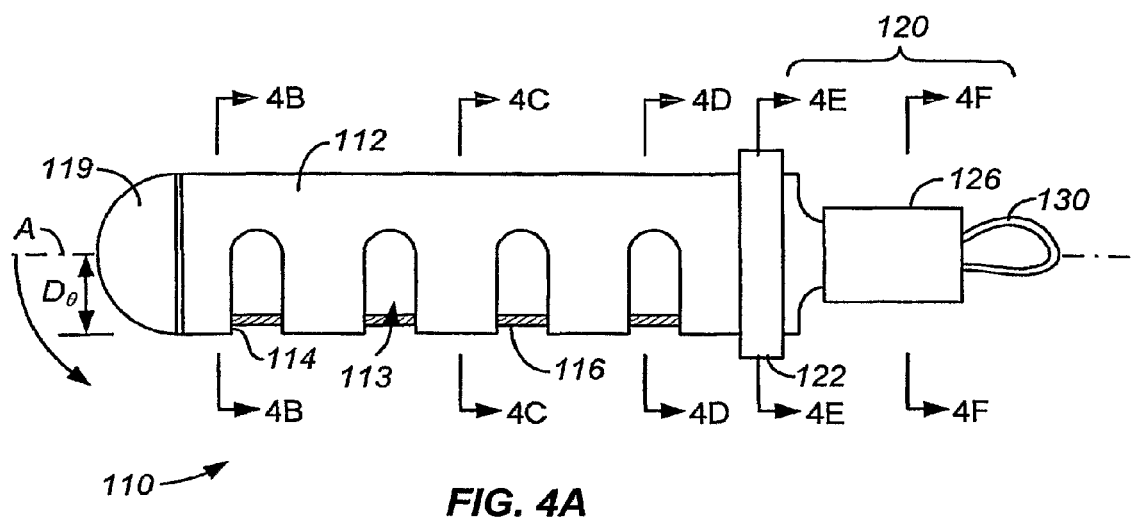
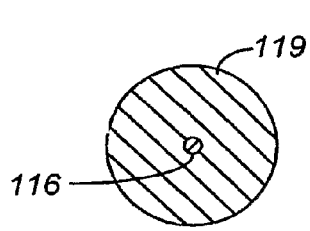 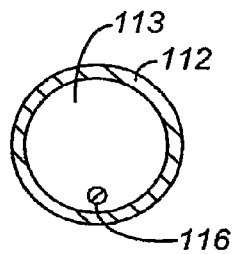 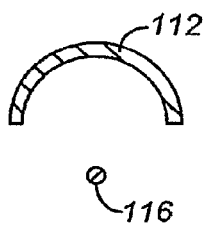
FIG. 4B    FIG. 4C    FIG. 4D
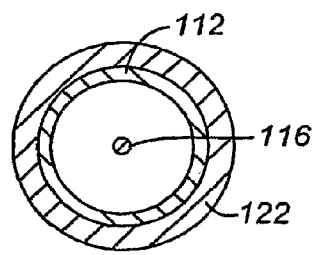 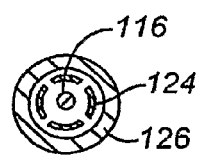
FIG. 4E    FIG. 4F

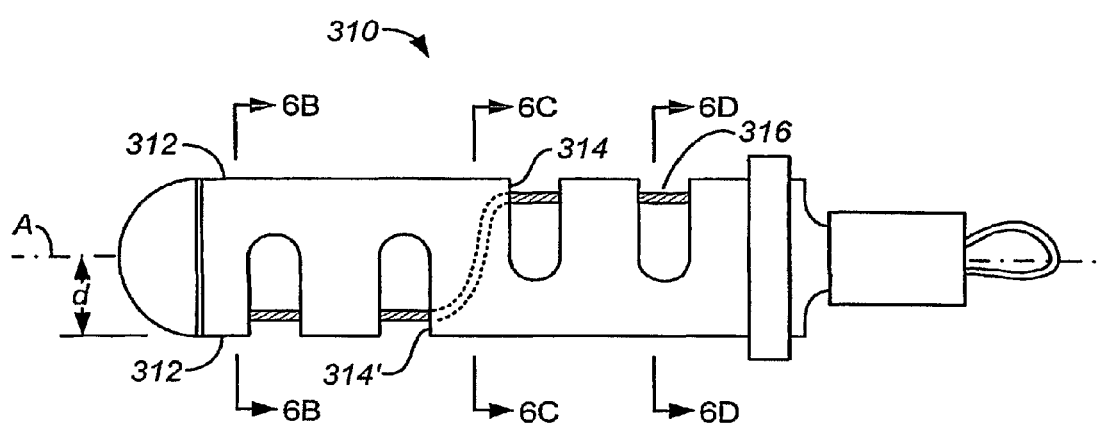
FIG. 6A
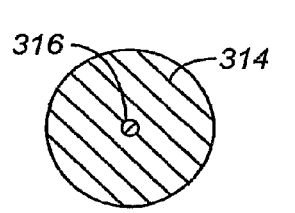 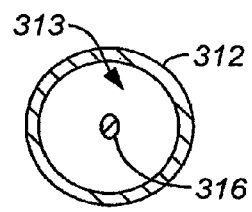 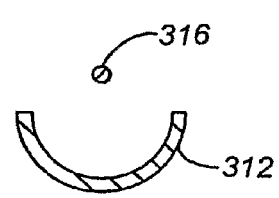
FIG. 6B   FIG. 6C   FIG. 6D

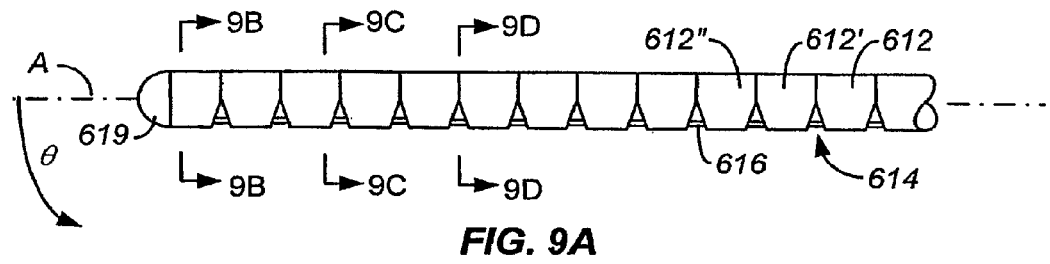
FIG. 9A
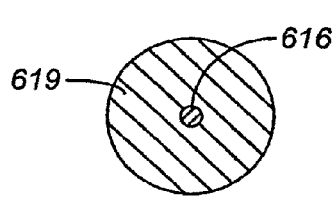
FIG. 9B
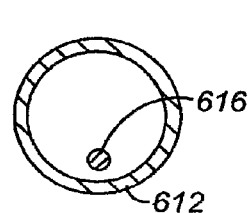
FIG. 9C
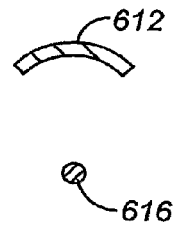
FIG. 9D
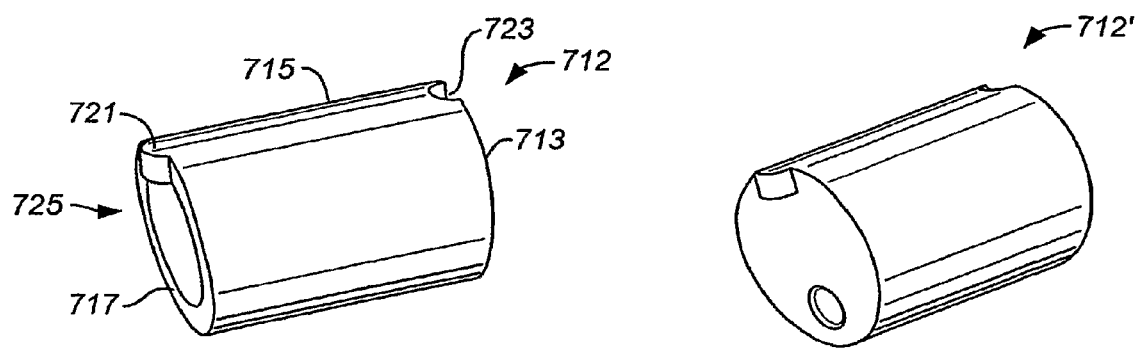
FIG. 10A  FIG. 10B

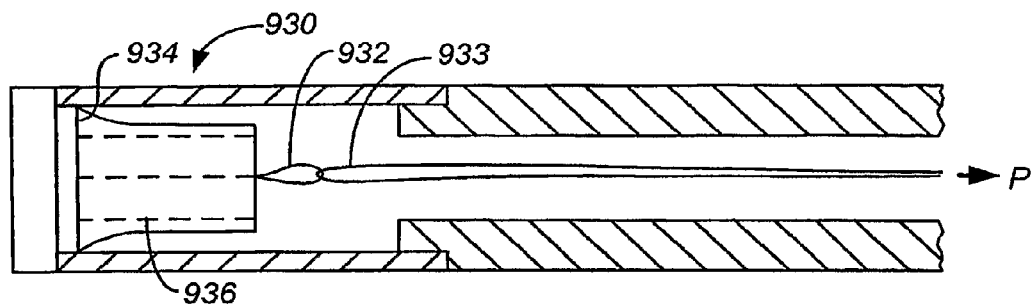
FIG. 12
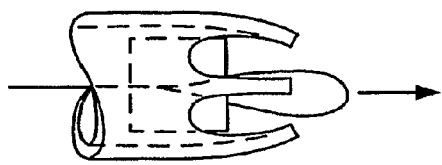
FIG. 13A
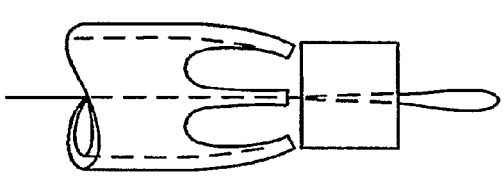
FIG. 13B
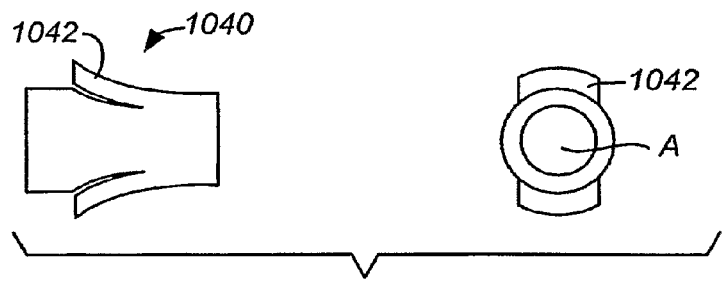
FIG. 14A
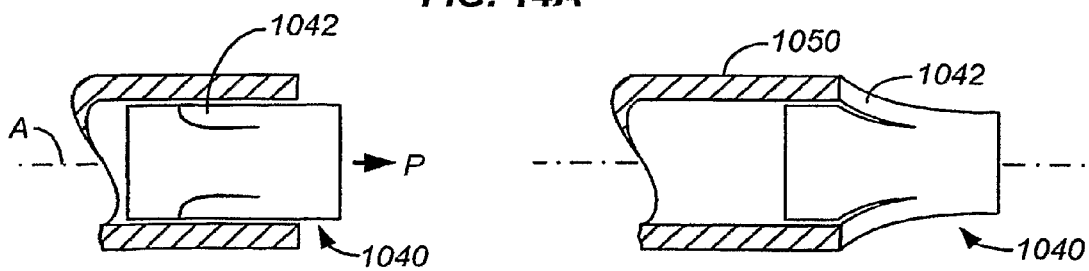
FIG. 14B
FIG. 14C

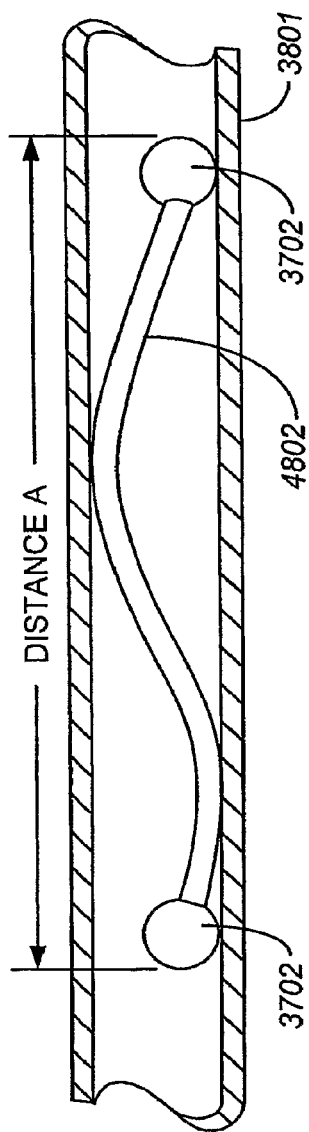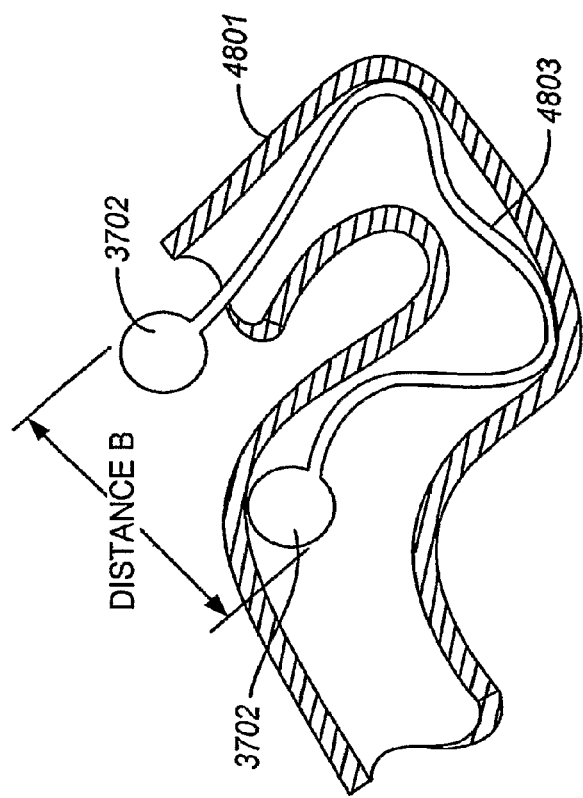

MINIMALLY INVASIVE LUNG VOLUME REDUCTION DEVICES, METHODS, AND SYSTEMS

CROSS-REFERENCES TO RELATED APPLICATIONS

This application is a continuation application of PCT Patent Application No. PCT/US2007/006339, filed internationally on Mar. 13, 2007, which is a continuation-in-part of U.S. patent application Ser. No. 11/422,047, now U.S. Pat. No. 8,157,837, entitled Minimally Invasive Lung Volume Reduction Device and Method, filed Jun. 2, 2006, which is incorporated herein by reference in its entirety and to which application we claim priority under 35 U.S.C. §120.

This application claims the benefit of U.S. Provisional Patent Applications 60/743,471, entitled Minimally Invasive Lung Volume Reduction Device and Method, filed on Mar. 13, 2006; 60/884,804, entitled Minimally Invasive Lung Volume Reduction Devices, Methods and Systems, filed Jan. 12, 2007; and 60/885,305, entitled Minimally Invasive Lung Volume Reduction Devices, Methods and Systems, filed Jan. 17, 2007, under 35 U.S.C. §365, each of which are incorporated herein in their entirety.

BACKGROUND OF THE INVENTION

1. Field of the Invention

Devices, systems and methods are described for treating lungs. The devices, systems and methods improve the quality of life and restore lung function for patients suffering from emphysema. The systems consist of an implant and a delivery catheter that can be advanced through tortuous anatomy and actuated to retain a pre-determined shape and rigidity. The actuated implant modifies the shape of the airways and locally compresses lung parenchyma to cause volume reduction and thereby tensions the lung parenchyma to restore elastic recoil. Systems and devices are also included that deploy and actuate the implantable devices, as well as systems and devices designed for recapture of the implanted device.

2. Background of the Invention

Current medical literature describes emphysema as a chronic (long-term) lung disease that can get worse over time. It's usually caused by smoking. Having emphysema means some of the air sacs in your lungs are damaged, making it hard to breathe. Some reports indicate that emphysema is the fourth largest cause of mortality in the U.S., affecting an estimated 16-30 million U.S. citizens. Each year approximately 100,000 sufferers die of the disease. Smoking has been identified as a major cause, but with ever increasing air pollution and other environmental factors that negatively affect pulmonary patients; the number of people affected by emphysema is on the rise.

A currently available solution for patients suffering from emphysema is a surgical procedure called Lung Volume Reduction (LVR) surgery whereby diseased lung is resected and the volume of the lung is reduced. This allows healthier lung tissue to expand into the volume previously occupied by the diseased tissue and allows the diaphragm to recover. High mortality and morbidity may be associated with this invasive procedure. Several minimally invasive investigational therapies exist that aim at improving the quality of life and restoring lung function for patients suffering from emphysema. These potential therapies include mechanical devices and biological treatments. The Zephyr™ device by Emphasys (Redwood City Calif.) and the IBV™ device by Spiration (Redmond Wash.) are mechanical one way valve devices. The underlying theory behind these devices is to achieve absorptive atelectasis by preventing air from entering diseased portion of the lung, while allowing air and mucous to pass through the device out of the diseased regions.

The Watanabe spigot is another mechanical device that completely occludes the airway, thereby preventing air from entering and exiting the lung. Collateral ventilation (interlobar and intralobar—porous flow paths that prevent complete occlusion) prevents atelectasis and this is shown in the published Emphasys VENT clinical trial data, where approximately ⅓ or fewer of the patients actually achieve measurable atelectasis. The lack of atelectasis or lung volume reduction drastically reduces the effectiveness of such devices. Other mechanical devices include means of deploying anchors into airways and physically deforming airways by drawing the anchors together via cables.

Biological treatments utilize tissue engineering aimed at causing scarring at specific locations. Unfortunately, it can be difficult to control the scarring and to prevent uncontrolled proliferation of scarring.

SUMMARY OF THE INVENTION

An aspect of the invention includes a lung volume reduction system comprising an implantable device adapted to be delivered to a lung airway of a patient in a delivery configuration and to change to a deployed configuration to bend the lung airway. The system has a delivery configuration that is resiliently bendable into a plurality of shapes. The system can have a deployed configuration that has a rigid shape. Additionally, the system may be elastically strained into a deliverable shape whereby elastic recoil allows it to recover back to its manufactured shape that provides a load on lung tissue. Further shapes include: c-shape; S-shape; and Spiral, baseball seam shape to name a few.

The system can further be adapted to comprise an actuator adapted to be operated from outside the patient to change the implantable device from the delivery configuration to the deployed configuration. The actuator comprises an actuation element connected to a distal end of the implantable device and adapted to be moved proximally to bend the device. As will be appreciated by those skilled in the art, the distal end includes the front end of the device and can include, for example, from the mid-point along the length to the end furthest away from the user.

In some embodiments, the system can further be adapted to comprise a lock adapted to lock the device in the deployed configuration. In some embodiments, the lock comprises a ratchet. In other embodiments, the lock can be unlocked for retrieval. The system can further comprise a connector adapted to connect the implantable device to the actuator and to disconnect the device from the actuator after actuation. The connector may be used to connect two or more devices together. The device can be configured to comprise a member having a plurality of notches adapted to permit the device to bend more easily in one direction than in another. In some embodiments, the device can further be adapted to self-actuate from the delivery configuration to the deployed configuration. The devices of the invention can be comprised of shape memory material. Suitable shape memory material are known in the art and include the nickel-titanium alloy Nitinol. In some embodiments a plurality of shape memory elements can be configured to form a flexible overtube. In other embodiments, the device comprises a plurality of asymmetric segments and a connecting element adapted to connect the segments. In still other embodiments, the device is adapted to be delivered through a working channel of a bronchoscope. In still other embodiments, the device is adapted to be delivered from a loading cartridge through a catheter that is adapted to fit through a working channel of a bronchoscope. The system may include a guide wire for steering to specific bronchi, a wire steering handle to assist with grasping the wire to rotate it, a dilator to provide a smooth transition from the wire to a delivery catheter and a loading cartridge to contain the implant system in a deliverable condition. The device can further be adapted to provide an anchor to anchor the device within the airway. In still other embodiments, the system further comprises a delivery tool adapted to deliver the device to a treatment site in the airway. In yet other embodiments, the system further comprises a retrieval tool adapted to retrieve the device from the airway after delivery. The retrieval device can further be adapted to unlock the device from the deployed configuration. As will be appreciated by those skilled in the art, the device can be configured to have a fixed length or a variable length.

A method of bending a lung airway of a patient is also provided. The method comprising inserting a device into the airway in a delivery configuration and bending the device into a deployed configuration, thereby bending the airway. In some embodiments of the method, the bending step comprises operating an actuator outside the patient, the actuator being operatively connected to the device. The method further comprises locking the device into the deployed configuration. The method can also comprise unlocking the device to permit it to return to the delivery configuration. In yet other embodiments, the method can include disconnecting the actuator from the device. In some instances, the device comprises a plurality of asymmetric segments, inserting comprises delivering the plurality of asymmetric segment to the airway. In still other embodiments, the bending comprises rotating at least one asymmetric segment with respect to at least another asymmetric segment. In some instances, the device comprises shape memory material, bending comprises permitting the device to bend itself. The method can also further comprise the step of delivering an overtube and subsequently delivering a shape memory element to the overtube. Depending upon the desired result, the bending can comprise bending the device into a substantially C shape; bending the device into a substantially S shape; or bending the device into a substantially spiral shape. Additionally, the inserting step can further comprise delivering the device through a working channel of a bronchoscope. In yet other embodiments, the device can be elastically strained into a deliverable shape, advanced through and out the end of a bronchoscope whereby elastic recoil drives the system, to recover back to it's original manufactured shape. Finally, the method can further comprise the step of retrieving the device from the airway.

The design of the device facilitates strain relief on both ends of the device. Further the ends of the device in either the delivery or deployed state are more resilient.

The implant length can range from, for example, 2 cm to 10 cm. Typically, the length is 5 cm. The diameter of the device can range from 1.00 mm to 3.0 mm, preferably 2.4 mm. The device is used with a catheter which has a working length of 60 cm to 200 cm, preferably 90 cm.

Suitable materials for use in constructing the implant, delivery or retrieval systems include materials selected from: metals (stainless steel, nickel-titanium alloy (Nitinol), titanium); polymers (durable and bioabsorbable); ultra high molecular weight polyethylene (UHMWPE), polycarbonate, silicone, urethane, Teflon® (available from DuPont), fluoropolymers, Poly (d, 1-lactic-co-glycolic acid), poly(glycolic acid caprolactone), [rho]oly(lactide co-glycolides), as well as any other material that would be considered suitable by a person of skill in the art. Other materials include polymers (nylon, Pebax®, polyetheretherketone (PEEK), polycarbonate, Acrylonitrile Butadiene Styrene (ABS), high density polyethylene, low density polyethylene, polypropylene, polyimide, urethane, polyethylene, and terephthalate), as well as any other material that would be considered suitable by a person of skill in the art. One or more materials can be employed in any of the embodiments described.

In one embodiment, the device is constructed from a metallic or polymeric tube with slots separated by specific distances that allow preferential bending of the tube where the slots are oriented. In another embodiment, the implant is composed of short segments of metallic or polymeric tubes or cylinders.

Aspects of the invention also include devices adapted to deliver and/or retrieve the implant. The device can be configured to pull or push the actuation device; lock the device in a particular configuration; unlock the device; maintain the device at a temperature that facilitates implantation; manipulates the proximal end of the device to facilitate retrieval; and/or controls the torque on the device.

The delivery catheter construction includes a stainless steel hypotube, stainless steel tight-pitch coil, polymeric tube (polyimide, Nylon, Pebax® (available from Ato Chimie), Teflon®, fluoropolymers) with stainless steel reinforcement (braided, axial).

In operation the devices of the invention are minimally invasive and can be used with a bronchoscope procedure. There is no incision, and no violation of the pleural space. Collateral ventilation does not affect the effectiveness. The devices can be used for homogeneous and heterogeneous emphysema.

In yet another embodiment of the invention, the lung volume reduction system comprises an implantable device that imparts bending force on lung tissue. The lung volume reduction system can further be adapted and configured to comprise an implantable spring element that imparts bending force on lung tissue. In yet another embodiment of the invention, a lung volume reduction system is adapted and configured to comprise an implantable spring element that can be constrained into a shape that can be delivered to a lung airway and unconstrained to allow the element to impart bending force on the airway to cause the airway to be bent.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37 degrees Celsius or colder. Additionally, at least a portion of the metal of the device can be transformed to the martensite phase in the delivery configuration and/or can be in an austenite phase condition in the deployed configuration.

In another embodiment of the invention, a lung volume reduction system comprising an implantable device that is configured to be deliverable into a patient's lung and configured to be reshaped to make the lung tissue that is in contact with the device more curved. In some embodiments, The device is configured to be reshaped to a permanent second configuration. Additionally, or alternatively, the device can be adapted and configured to have a first shape and is configured to be strained elastically to a deliverable shape. Additionally, in some embodiments, the implantable device has a first shape and is adapted to be elastically constrained by a delivery device to a deliverable configuration whereby removal of the delivery device allows the implant to recoil and be reshaped closer to its first shape. In still other embodiments, the tissue that is in contact with the device is that of blood vessel, airway, lung dissection fissure or a combination of these. The delivered device can be reshaped into a shape that is shorter in length than the deliverable implant configuration. Additionally, the implant can be adapted and configured to provide a distal end and a proximal end and the distance between the two ends is reduced when the implant is reshaped. Further, the implant can be configured to occupy less than the entire lumen cross section area of a lung airway; less than the entire lumen cross section area of a blood vessel; and/or have a deliverable shape that fits within a cylindrical space that is 18 mm in diameter or smaller. In some embodiments, the surface area of the implant that comes into contact with tissue is larger than $1.0^{-6}$ square inches per linear inch of length of the implant. In other embodiments, the implant is coated with material that reduces the rate of wound healing, tissue remodeling, inflammation, generation of granular tissue or a combination of these. In still other embodiments, the reshaped implant is adapted and configured to lie within a single plane. Additionally, the reshaped implant can take on a variety of shapes, including, for example, the shape of a C, the shape of an S, or any other suitable shape. In still other embodiments, the reshaped implant is adapted and configured to lie within more than a single plane. In multiplanar embodiments, the reshaped implant is adapted and configured to take on a variety of shapes, including, for example, the shape of a baseball seam, or the shape of a coil. In some embodiments, the reshaped implant has more than one radius of curvature. Additionally, systems are provided wherein more than one implant is delivered and reshaped. In such systems, the devices can be delivered to separate locations. Alternatively, the devices can be coupled, either before or after delivery. Additionally, the implants can be deployed to partially occupy a common region in the lung. In still further embodiments, the lung volume reduction system can provide implantable devices made of a resiliently bendable material. The system can further be adapted to comprise an actuator adapted to be operated from outside the patient to reshape the implant. Suitable mechanisms for actuating the device include, catheters. Additionally, the catheter can be further adapted and configured to constrain the implant in a deliverable configuration. In some embodiments, the system further comprises a pusher adapted to deliver the implant into a patient's lung. Additionally, the implant can be adapted and configured to have blunt distal and proximal ends, such as with the use of balls positioned thereon. Additionally, a central wire can be provided that spans the length of the device. A pusher can be provided that is releasably coupled to the device.

In another embodiment, the system provides a recapture device adapted and configured to remove the implant from a patient's lungs. The recapture device can be adapted to couple at an end of the device. Additionally, the recapture device can be configured to operate within a catheter or bronchoscope working channel lumen. A resilient wire can also be provided to guide a delivery catheter. In still other embodiments, the system further comprises a resilient dilator device that fits in the catheter lumen. The dilator device can be further adapted and configured to provide a lumen that accommodates a resilient wire. In at least some embodiments, the lung volume reduction system implant has an arc length that remains constant.

In yet another embodiment of the invention, a lung volume reduction device is provided that comprises an elongate body adapted to be inserted into a lumen adjacent lung tissue, the device having a delivery configuration and a deployed configuration more curved than the delivery configuration. In some embodiments, the elongate body is more rigid in the deployment configuration than in the delivery configuration. In still other embodiments, at least a portion of the elongate body comprises a rigid arc when in the deployment configuration having rigidity greater than that of lung tissue. In some embodiments, the rigid arc extends from a point in a proximal half of the device to a point in the distal half of the device. In still other embodiments, the elongate body comprises a plurality of rigid arcs when in the deployment configuration. The plurality of rigid arcs can also be positioned such that the arcs are not at the proximal or distal ends of the elongate body.

In another embodiment of the invention, a lung volume reduction system is provided comprising an implantable device that is configured to be deliverable into a patient's lung and configured to reshape lung tissue while allowing fluid to flow both directions past the implant.

In still another embodiment of the invention, a lung volume reduction system is provided comprising an implantable device that is configured to be deliverable into a patient's lung configured to be reshaped to a shape that is not axi-symmetric to bend lung tissue.

According to a method of the invention, a method of reducing a patient's lung volume is provided comprising: inserting a lung volume reduction device into a patient lumen, such as a lung airway, adjacent lung tissue in a delivery configuration, the device comprising an elongate body; and moving the elongate body from the delivery configuration to a deployment configuration more curved than the delivery configuration. The step of moving can further comprise making at least a portion of the elongate body more rigid. In another embodiment, the step of moving can comprise forming a rigid arc in the elongate body, the rigid arc having a rigidity greater than that of the lung tissue. In yet another embodiment, the step of moving can further comprise forming a plurality of rigid arcs in the elongate body. In still another embodiment, the step of moving can further comprise forming the plurality of rigid arcs away from a proximal end or a distal end of the elongate body.

Pursuant to another method of the invention, a method of bending a lung airway of a patient is provided comprising inserting a device into the airway in a delivery configuration and bending the device into a deployed configuration to reduce the radius of curvature of at least a portion the airway.

Still another method of the invention provides a method of bending a lung airway of a patient comprising inserting an implantable device into the airway in a delivery configuration and bending the device into a deployed configuration to reduce the radius of curvature of at least a portion the airway. In an embodiment, the step of bending can further comprise operating an actuator outside the patient, the actuator being operatively connected to the device. In yet another embodiment, the step of bending further comprising locking the device into the deployed configuration. In still another embodiment, the step of bending further comprises unlocking the device to permit it to return to the delivery configuration. Additionally, in some embodiments, the step of bending can further comprise disconnecting the actuator from the device. Suitable devices for the methods of the invention include devices that comprise a plurality of asymmetric segments, inserting comprises delivering the plurality of asymmetric segments to the airway as well as devices comprising shape memory material. Additionally, the step of bending can further comprise rotating at least one asymmetric segment with respect to at least another asymmetric segment. An additional step of some embodiments of the method can further comprise delivering a catheter and delivering a shape memory element through the catheter. After delivery of the device, according to the methods provided, the device can then bend into a substantially C shape, S shape, spiral shape, coil shape of one or more radiuses, as well as any shape that is within one or more planes. In an additional embodiment of the method, the step of inserting further comprises delivering the device through a working channel of a bronchoscope. In yet another step of the method, the method further comprises retrieving the device from the airway. Embodiments of the method can further provide the step of providing strain relief to an end of the device during deployment. The delivery configuration of the device can be achieved by transforming metal to a martensite phase or by cooling the implant, such as by delivering liquids or gas. Cooled liquids or gases can be at delivered at temperatures that are at or below body temperature, are 37 degrees Celsius or lower in temperature, or at or below zero degrees Celsius. In some methods of the invention, the implant and surrounding tissues are cooled below zero degrees Celsius, or at or below minus fifteen degrees Celsius.

In yet another method of the invention, a method of reducing lung volume by bending a lung airway of a patient is provided comprising inserting an implantable device into the airway in a delivery configuration and bending the device into a deployed configuration to change the radius of curvature of at least a portion of the airway.

In another method of the invention, a method is provided for reducing lung volume in a patient comprising inserting a device into an airway and causing bending of the airway. The method can further include the step of inserting a second device into a second airway; connecting the first and second devices to each other; bending the first device to a the first device to a deployed condition to bend or deform the airway at a first location; and bending the second device to a deployed condition to bend the airway at a second location. Additionally, the method can include connecting two or more devices, such as connecting the devices to a common airway. An additional step of the method can include applying pressure on the junction where the airways join. Still another step of the method can include connecting bending elements that are individually placed into one or more airways. Yet another step can include bending one or more bending elements that are placed in one or more airways. An additional step includes configuring the device to make the airway conform to the shape of the implant in a deployed condition.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the present invention will be obtained by reference to the attached documents that set forth illustrative embodiments, in which the principles of the invention are utilized, and the accompanying drawings of which:

FIGS. 4A-F illustrate a lung volume reduction device according to an aspect of the invention;

FIGS. 6A-D illustrate a lung volume reduction device according to another aspect of the invention;

FIGS. 9A-D illustrate a lung volume reduction device according to another aspect of the invention;

FIGS. 10A-B illustrate segments suitable for use in configuring a lung volume reduction device according to an aspect of the invention;

FIG. 12 illustrates a lock feature suitable for use at a proximal end of a lung volume reduction device;

FIGS. 13A-B illustrate a stopper adapted to hold tension on a lung volume reduction device;

FIGS. 14A-C illustrates a self locking mechanism suitable for use with the lung volume reduction devices of the invention;

FIG. 47 illustrates a length change from delivery to deployed;

FIG. 48 illustrates a system with bronchoscope, catheter, dilator, wire and a wire steering handle;

DETAILED DESCRIPTION OF THE INVENTION

Figure 1A:
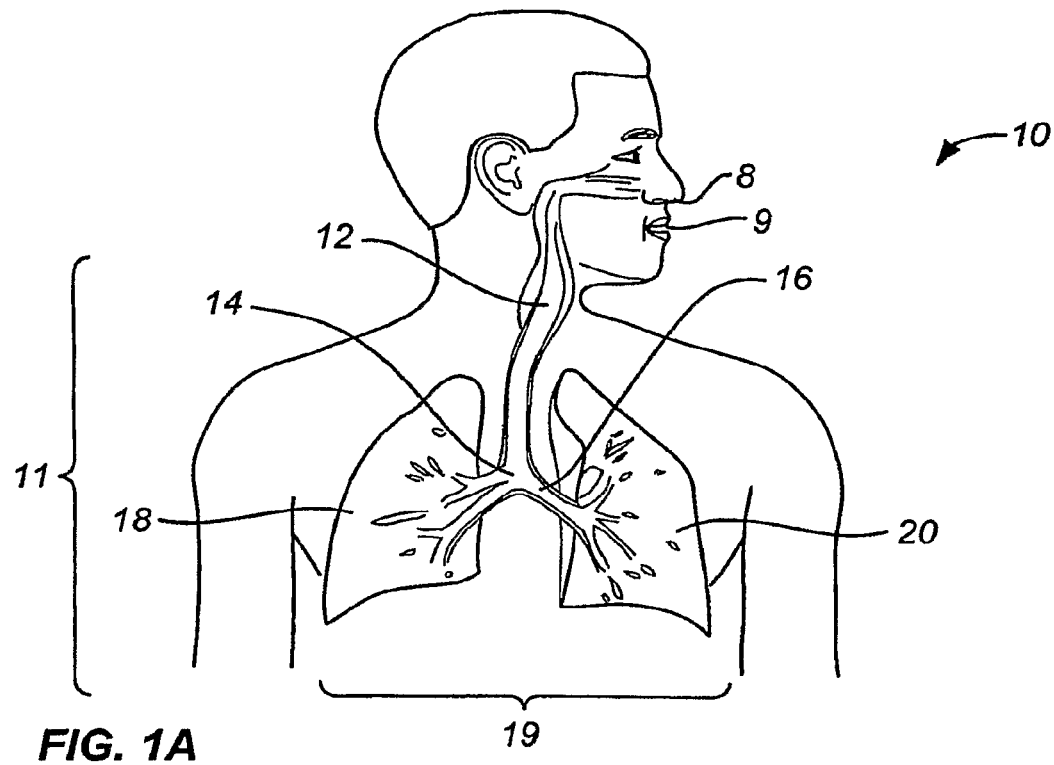
FIGS. 1A-C illustrates the anatomy of the respiratory system.

By way of background and to provide context for the invention, FIG. 1A illustrates the respiratory system 10 located primarily within a thoracic cavity 11. This description of anatomy and physiology is provided in order to facilitate an understanding of the invention. Persons of skill in the art, will appreciate that the scope and nature of the invention is not limited by the anatomy discussion provided. Further, it will be appreciated there can be variations in anatomical characteristics of an individual, as a result of a variety of factors, which are not described herein. The respiratory system 10 includes the trachea 12, which brings air from the nose 8 or mouth 9 into the right primary bronchus 14 and the left primary bronchus 16. From the right primary bronchus 14 the air enters the right lung J 8; from the left primary bronchus 16 the air enters the left lung 20. The right lung 18 and the left lung 20, together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
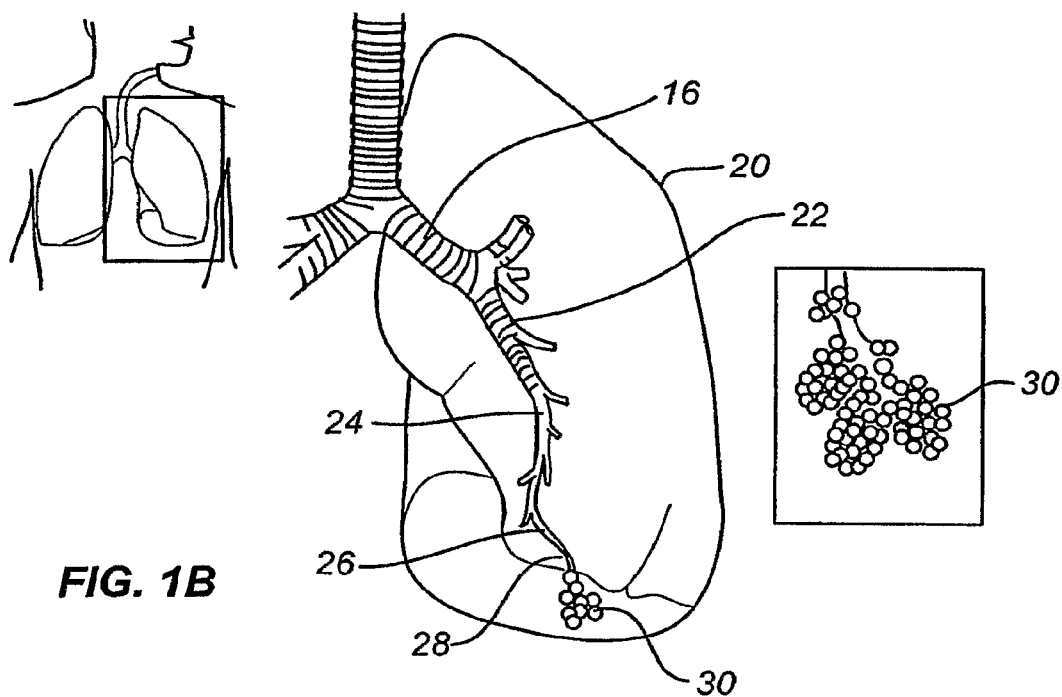
Figure 1C:
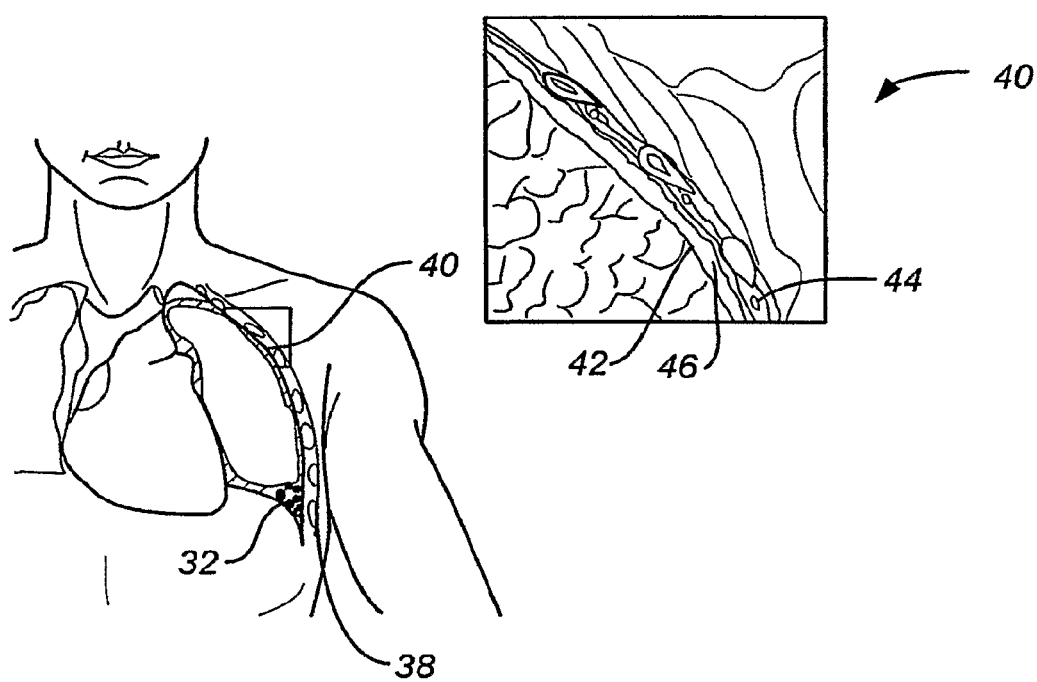
Figure 2A:
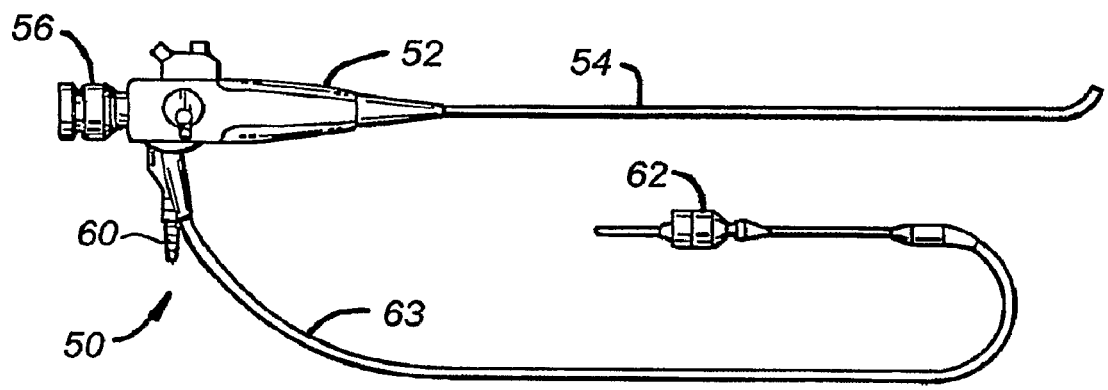
FIGS. 2A-D illustrate a bronchoscope.
Figure 2B:
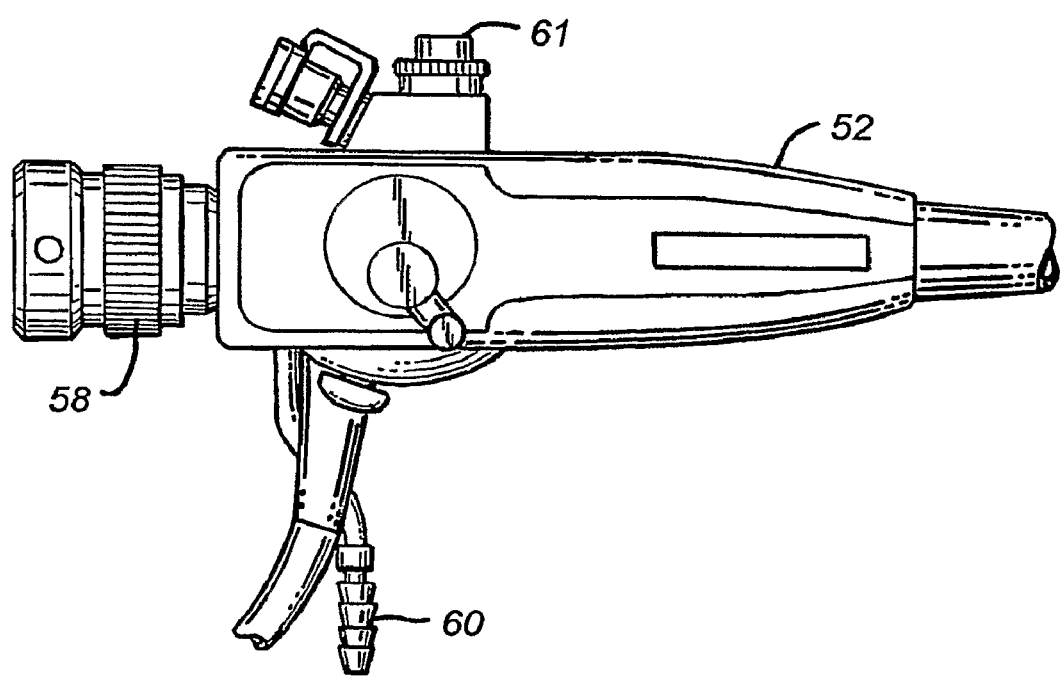
Figure 2C:
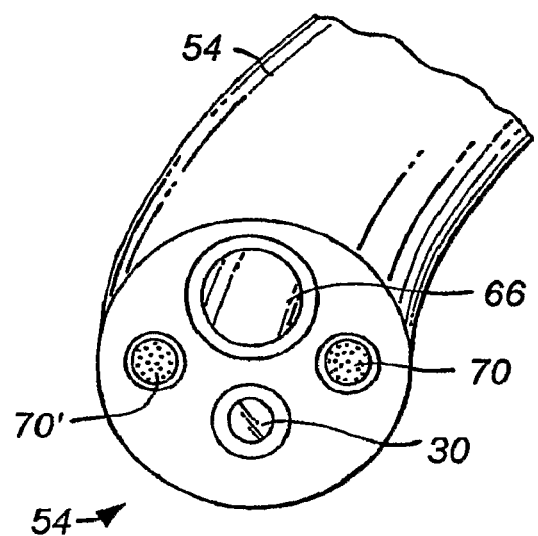
Figure 2D:
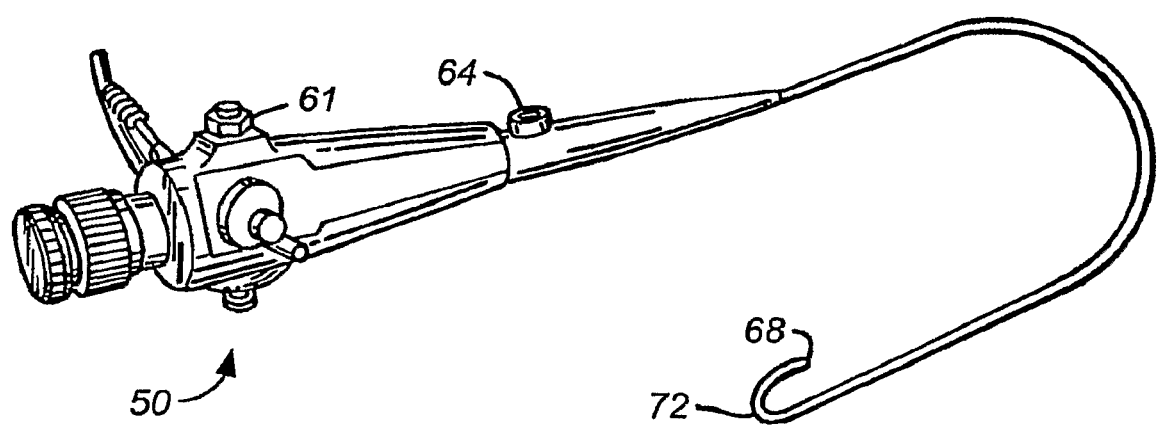

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38 protects the lungs 19 and allows the lungs to move during breathing. As shown in FIG. 1C, the pleura. 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are described in current literature an elastic structure that float within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42. As discussed above, when the air sacs in the lungs are damaged 32, such as is the case with emphysema, it is hard to breathe. Thus, isolating the damaged air sacs to improve the elastic structure of the lung improves breathing.

A conventional flexible bronchoscope is described in U.S. Pat. No. 4,880,015 to Nierman for Biopsy Forceps. As shown in FIGS. 2A-D, bronchoscope 50 can be configured to be of any suitable length, for example, measuring 790 mm in length. The bronchoscope SO can further be configured from two main parts, a working head 52 and an insertion tube 54. The working head 52 contains an eyepiece 56; an ocular lens with a diopter adjusting ring 58; attachments for the suction tubing 60 and a suction valve 61 and for the cold halogen light source 62 and 63; and an access port or biopsy inlet 64, through which various devices and fluids can be passed into the working channel 66 and out the distal end of the bronchoscope. The working head is attached to the insertion tube, which typically measures 580 mm in length and 6.3 mm in diameter. The insertion tube can be configured to contain fiberoptic bundles (which terminate in the objective lens 30 at the distal tip 68), two light guides 70, 70' and the working channel 66. The distal end of the bronchoscope has the ability to bend 72 anterior and posterior only, with the exact angle of deflection depending on the instrument used. A common range of bending is from 160 degrees forward to 90 degrees backward, for a total of 250 degrees. Bending is controlled by the operator by adjusting an angle lock lever 74 and angulation lever 76 on the working head. See also, U.S. Patent Pub.

US 2005/0288550 A1 to Mathis for Lung Access Device and US 2005/0288549 A1 to Mathis for Guided Access to Lung Tissue.

Figure 3:
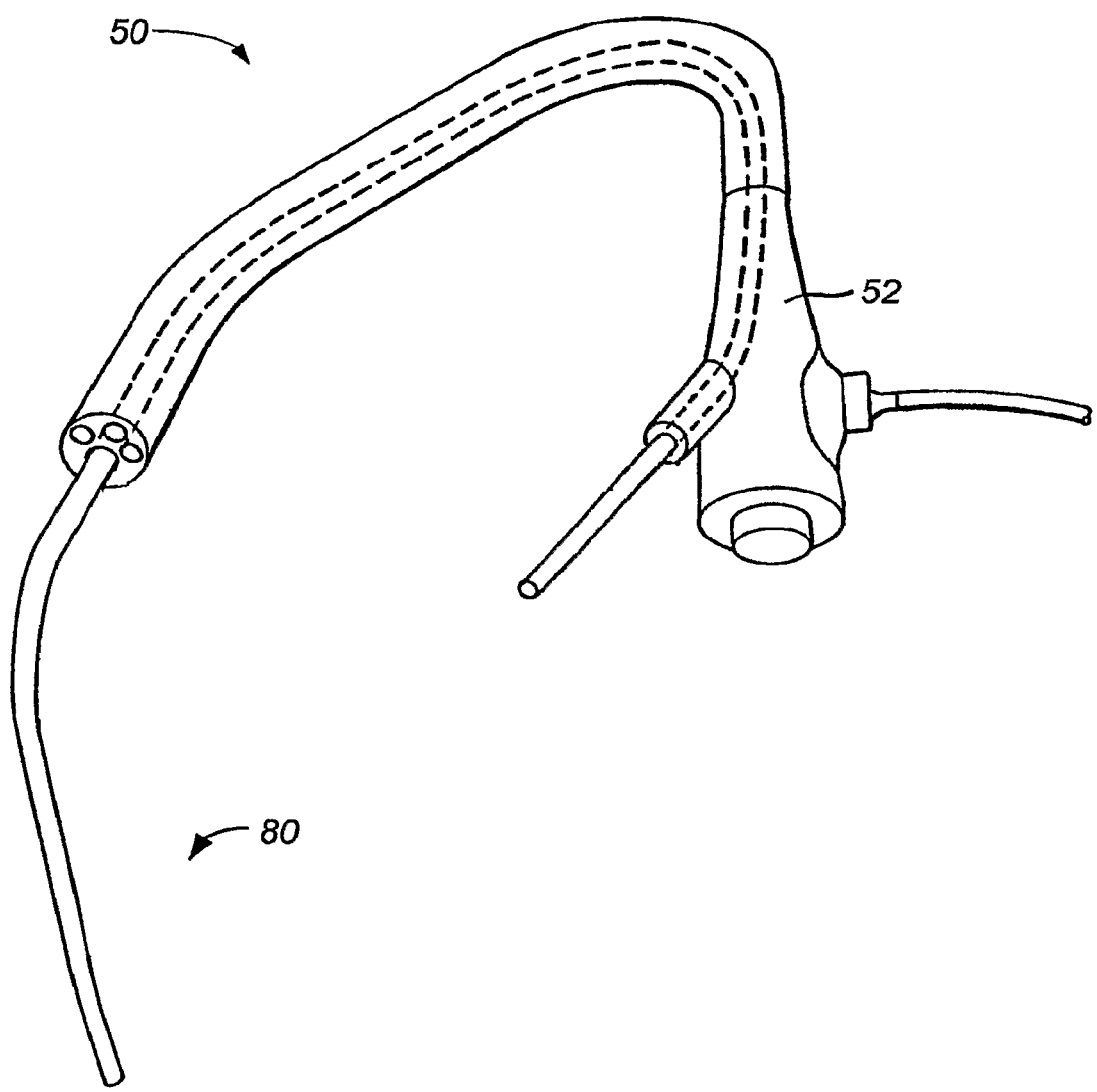
FIG. 3 illustrates a bronchoscope in combination with a delivery device for a lung volume reduction device according to the invention.

FIG. 3 illustrates the use of a lung volume reduction delivery device 80 for delivering a lung volume reduction device comprising an implantable device with the bronchoscope 50. The lung volume reduction system, as described in further detail below, is adapted and configured to be delivered to a lung airway of a patient in a delivered configuration and then changed to a deployed configuration. By deploying the device, tension can be applied to the surrounding tissue which can facilitate restoration of the elastic recoil of the lung. The device is designed to be used by an interventionalist or surgeon.

FIGS. 4A-F illustrate a lung volume reduction device 110 according to an aspect of the invention, with FIGS. 4B-F being cross-sections taken along the lines B-B, C-C, D-D, E-E and F-F of FIG. 4A, respectively. The lung volume reduction device JiO includes a member, such as tubular member 112, which has c-cuts 114, or notches, along its length to provide flexibility such that the device can be deflected off a longitudinal axis A when deployed. For example, where the cuts are oriented parallel each other along the length of the tubular member and are of the same or similar depth D, the device will tend to uniformly curve around an axis point when deployed (depicted below). As a result, the device preferentially curls or bends in a direction as determined by the shape of the slots. Different types (width, depth, orientation, etc.) of notches or slots can be used to achieve different operational effects and configurations of the deployed device without departing from the scope of the invention.

Positioned within a lumen 113 of the tubular member 112 is an actuation element 116 or pull-wire. The actuation element can have a circular circumference in cross-section, as depicted, or can have any other suitable cross-section. The actuation element 116 is anchored at one end of the device 110, e.g. the distal end, by a cap 119. The cap 119 can be bonded to the catheter and a distal crimp can be provided to crimp the cap into the pull wire. The rounded cap can also be provided to make the tip of the device atraumatic. The opposing end, e.g. proximal end, is adapted and configured to engage a mechanism 120. The mechanism enables the device to be deployed. The mechanism can further be adapted and configured to enable the device to lock into a deployed configuration once the device 110 is deployed or unlocked to retrieve the device. The device 110 is configured to be detachable from a delivery catheter adapted to deliver the lung volume reduction device (discussed below).

Mechanism 120, at the proximal end of the device, can be adapted to include a retainer ring 122 that engages a ratchet 124 that can be used to lock the device in place. The coupler 126 retains the ratchet 124 such that the ratchet locks the device in place once deployed. At the proximal end a retrieval adapter 130 is provided, such as a pull-wire eyelid. The retrieval adapter 130 is adapted and configured to enable the device to be retrieved at a later point during the procedure or during a subsequent procedure. The ratchet device has flanges that extend away from a central axis when deployed to lock the device in place.

Figure 5A:
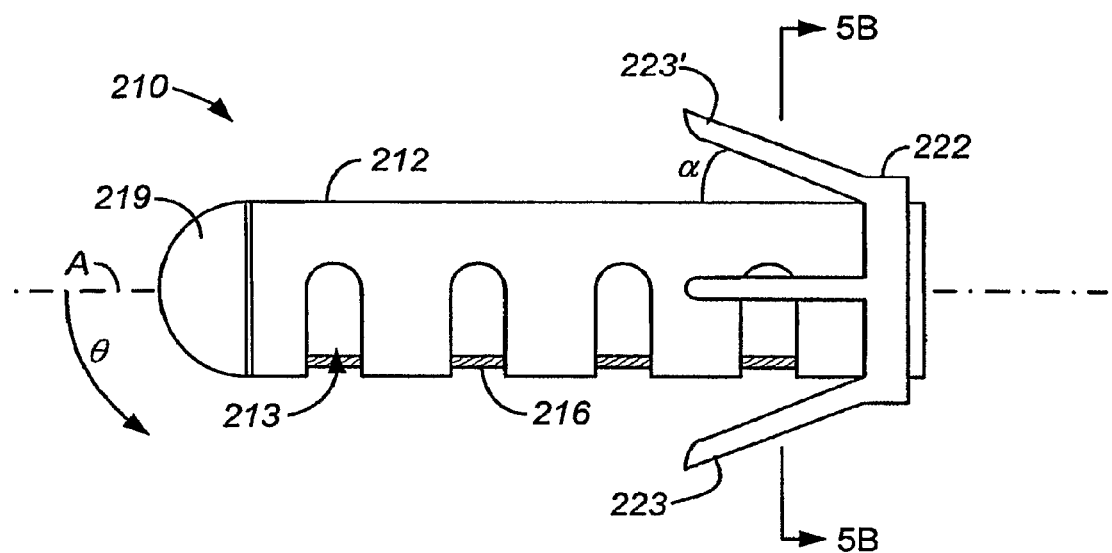
FIGS. 5A-B illustrate a lung volume reduction device according to another aspect of the invention.
Figure 5B:
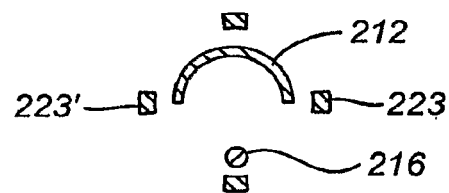

Turning to FIGS. 5A-B, a lung volume reduction device 210 according to another aspect of the invention is depicted, with FIG. 5B being a cross-section taken along the lines B-B of FIG. 5A. Positioned within a lumen 213 of the tubular member 212 is an actuation element 216 or pull-wire. As described above, the actuation element can have a circular circumference in cross-section, as depicted, or can have any other suitable cross-section. The actuation element 216 is anchored at one end of the device 210, e.g. the distal end, by a cap 219. In this embodiment, the retainer ring 222 is configured to provide anchors 223, 223' or teeth that are adapted to deploy by retracting the retaining sheath of a delivery catheter. When deployed, the anchors 223 contact the airway and affix the device in place. The anchor 223 can be configured to be self-expanding such that the anchors extend away from a central axis A of the device 210 when deployed until the anchors approach or extend through (e.g., hook) the airway. The amount of expansion of the anchors will be controlled by the design and the materials used. For example, where a shape memory material is used, the anchors can be configured to extend away from the longitudinal wall of the tubular member by a predetermined angle α, as depicted ~10 degrees. The design of the anchor can further be driven by the length of the device. The anchors can be configured to catch on the airway when deployed in a manner similar to the way a stent catches within the vasculature, or the anchor can be designed to cause friction. Prior to deployment, the anchors are retrained by a retaining sheath (illustrated below.).

FIGS. 6A-C illustrate yet another lung volume reduction device according to another aspect of the invention, with FIGS. 6B-C being cross-sections taken along the lines B-B, and C-C of FIG. 6A, respectively. As depicted in this embodiment, the lung volume reduction device 310 includes a member, such as tubular member 312, which has c-cuts 314, 314', or notches, along its length to provide flexibility such that the device can be deflected in more than one direction off a longitudinal axis A when deployed. In this embodiment, the notches are positioned on the member 312 on opposing sides of the member when the member is lying within a plane. For example, where the cuts are oriented parallel each other along the length of the tubular member and are of the same or similar depth D, the device will tend to uniformly curve around an axis point when deployed. In this embodiment, when deployed, the configuration of the notches would result in a deployed configuration that is "s"-shaped when the actuator element 316 is pulled proximally (i.e., toward the user).

Figure 7:
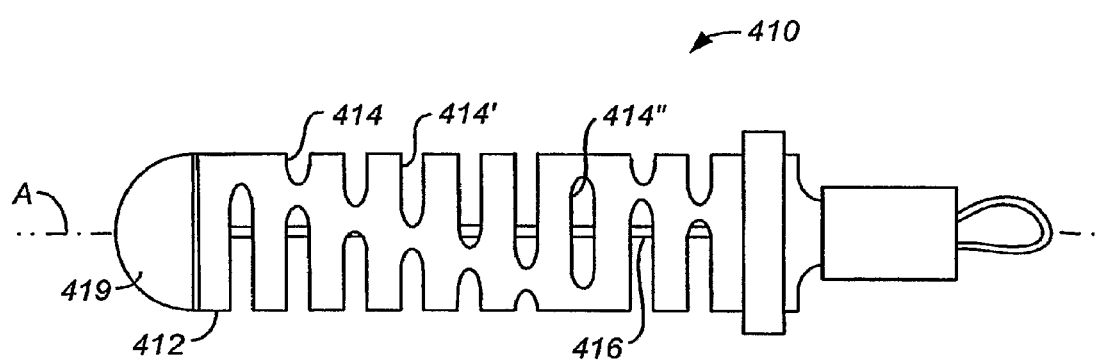
FIG. 7 illustrates a lung volume reduction device according to another aspect of the invention.

FIG. 7 illustrates yet another lung volume reduction device 410 according to another aspect of the invention. In this embodiment, the tubular member 412 has notches 414, 414', 414" configured in a spiral pattern along its length. As a result, when the actuation element 416 is pulled proximally toward the user, the device bends to form a spiral as illustrated below.

Figure 8:
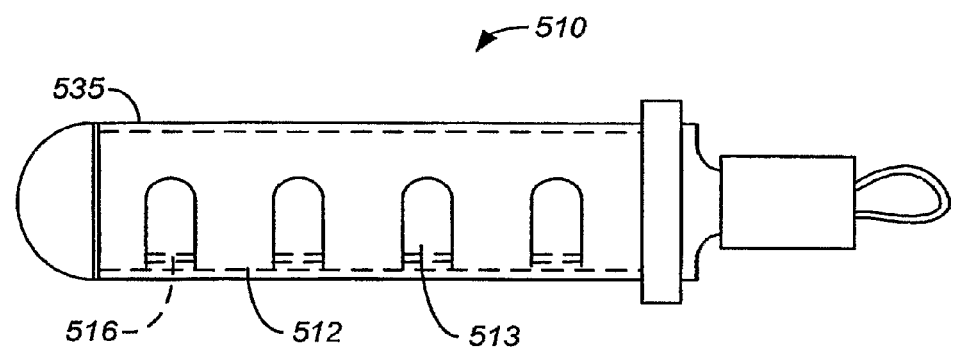
FIG. 8 illustrates a lung volume reduction device encased in a sheath.

FIG. 8 illustrates a lung volume reduction device SlO encased in a sheath 535. The sheath can be a polymeric elastic membrane, such as silicone. The sheath can prevent material from a body cavity from entering the lumen 513 of the tubular member 512. An actuation member 516 is provided within the lumen 513 of the tubular member 512.

FIGS. 9A-D illustrate yet another lung volume reduction device 610 according to another aspect of the invention, with FIGS. 9B-D being cross-sections taken along the lines B-B, C-C, and D-D of FIG. 9A, respectively. The lung volume reduction device 610 in this embodiment is comprised of individual segments 612, 612', 612". The segments can be configured, for example, to have identical asymmetrical configurations such that a compressible space 614 is between each segment before the device is actuated by activating the actuator element 616. Each of the segments can further comprise a detent on a first surface which opposes a mating indentation on a surface of an opposing segment. As will be appreciated, a variety of components of devices disclosed herein can be configured to provide locking or mating mechanisms to facilitate actuation and operation. When the actuation element 616 is activated, the compressible space is reduced and the opposing surfaces of two adjacent segments come together to reduce or eliminate the space between them, depending upon the desired outcome. Where the segments have identical or nearly identical configurations, the device will evenly arc around an axis point. Where the segments do not have identical configurations, a variety of configurations can be achieved upon deployment depending on the configurations of the segments selected and the organization of the segments in the device. As with previous embodiments, the actuator element 616 is secured at one end, e.g., the distal end, by a cap 619. The segments can be formed as hypotubes or can be formed as injection molded or solid pieces. Use of segments can avoid fatigue on the device because the surfaces come in contact with one another during compression. Material selection can also prevent biometallic corrosion. Further, the segment design is conducive for mass production and maintenance of consistence for final shape and operation.

FIGS. 10A-B illustrate segments 712, 712' suitable for use in configuring a lung volume reduction device according to an aspect of the invention. The segments, as depicted, can be generally cylindrical with a pair of surfaces that are either parallel or non-parallel each other at either end. To achieve the operation described above, a first surface 713 could be perpendicular to the elongated tubular sides 715 of the element, while the opposing surface 717 is not perpendicular to the sides of the element (or parallel to the opposing first surface). A detent 721 can be provided on one surface that is configured to mate with an indentation 723 the second surface of another. Other configurations, such as a key: keyway combination, can be used without departing from the scope of the invention. A central lumen 725 is provided through which an actuator element (described above) passes through.

Figure 11A:
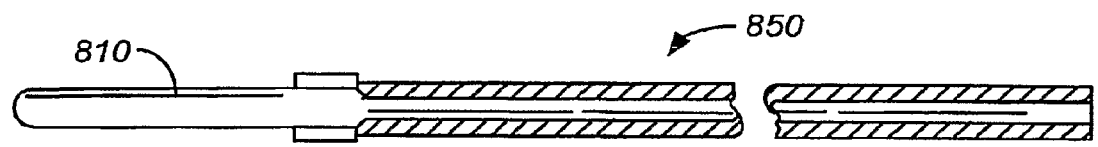
FIGS. 11A-F illustrate a plurality of individual wires formed of shape memory material that can be deployed to form a lung volume reduction device and a delivery device.
Figure 11B:
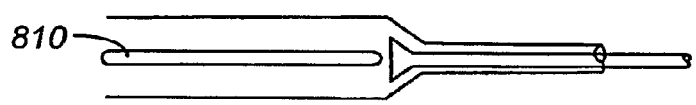
Figure 11C:
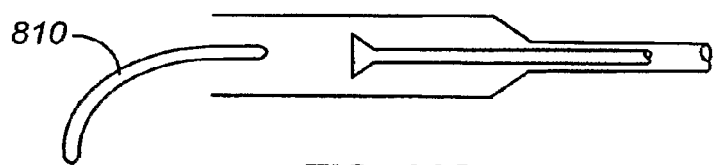
Figure 11D:
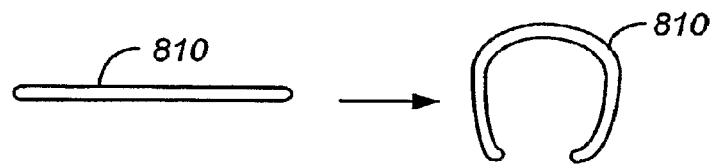
Figure 11E:
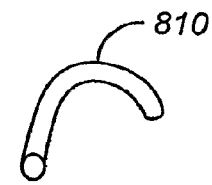
Figure 11F:
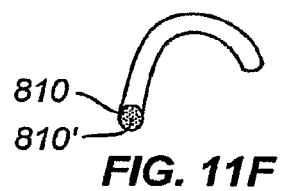

In another embodiment of the invention, as illustrated in FIGS. 11A-F, the device 810 is comprised of a plurality of individual wires formed of shape memory material that resume their shape when implanted. The wires can be heat treated to assume a specific shape, such as a C shape as described above. The wires are then individually implanted through a delivery system 850 such that when the first wire is implanted the diameter of the wire may be small enough that the wire cannot overcome the force applied by the surrounding tissue to assume its pre-configured shape. However, upon implantation of additional wires, the amount of strength available cumulatively among the wires does overcome the force applied by the tissue and the wires, together, achieve the desired shape (see. FIG. 11F). As will be apparent to those of skill in the art, the strength of a shaped wire can vary depending on how much material is used. For example, a shaped wire with a larger cross-section will have higher strength than a shaped wire with a smaller cross-section. However, a larger diameter wire may be harder to implant because it would be harder to straighten into a shape suitable for deployment. Where many small wires are used, each wire individually is more flexible and can be deployed easier, but as a larger number of wires are implanted the combined strength increases. In some embodiments, it may be useful to configure the devices 810 such that the use of, for example, 50-100 wires will have the strength to overcome pressure applied by the tissue. The wires 810 can be deployed within a flexible polymer tube to keep the wires in proximity to each other.

FIG. 12 illustrates a lock feature positioned at the proximal end of a lung volume reduction device such as those discussed above. The lock feature enables the deployed device to retain tension on the actuation element (e.g. 116) when the device is deployed. The lock mechanism 930 has an eyelid 932 which is adapted to engage a pull string 933. The lock feature normally rests on the inside of the implant and pops open to engage the tabs 934 when the ratchet 936 moves proximally P relative to the slotted tube. A stopper 940 can also be employed in the lung volume reduction devices. A stopper is depicted in FIG. 13. The stopper is adapted to hold the tension on the deployed device. Once the actuation element has been engaged and the desired amount of tension is applied which results in a desired shape of the device, the stopper can be deployed to maintain the tension on the device. The stopper can be configured as depicted with a slotted tube forming flanges 942 adapted to fit within a cap 944. Each of the flanges can be formed of shape memory material such that the flanges will tend to extend away from a central axis A to engage the interior surface of the cap 944.

Turning now to FIGS. 14A-C, a self-locking mechanism 1040 suitable for the proximal end of a lung volume reduction device of the invention is depicted, with FIGS. 14B-C being cross-sections taken along the lines B-B, and C-C of FIG. 14A, respectively. One or more flanges 1042 are provided. The flanges 1042 can be configured such that the flanges deflect away from a central axis A when not constrained. Thus, as shown in FIGS. 14B-C, the flanges 1042 are positioned to engage the sides of the of the self locking mechanism 1040. The flanges can be configured such that they form cut-outs that extend from the device, or can be integrally formed such that the self-locking mechanism still forms a solid tube when the flanges are deployed. FIG. 14c depicts the deployed flanges withdrawn from a retaining tube 1050 of the implant. The interference between the end of the flange and the sides of the retaining tube can be used to prevent, for example, the tap or ratchet from going back into the implant.

Figure 15A:
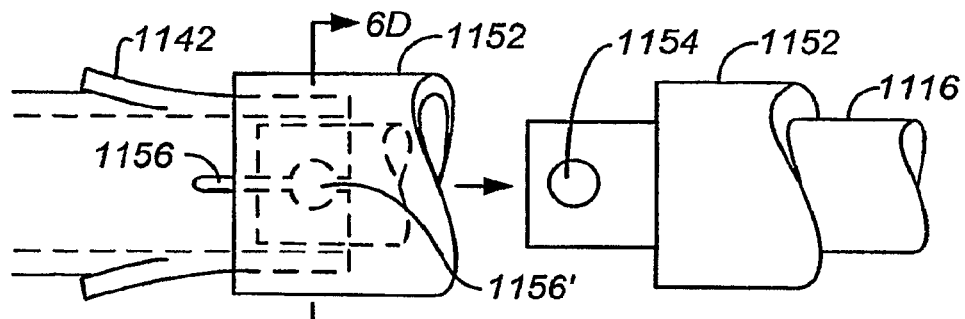
FIGS. 15A-D illustrate a decoupler system.
Figure 15B:
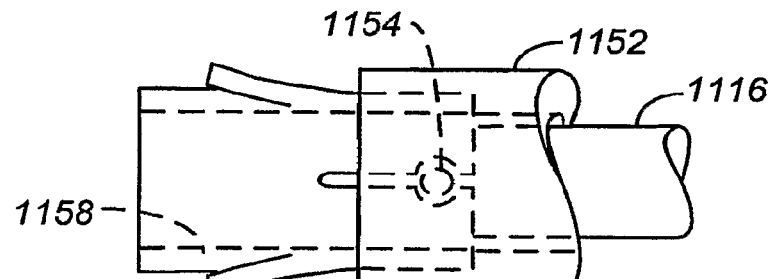
Figure 15C:
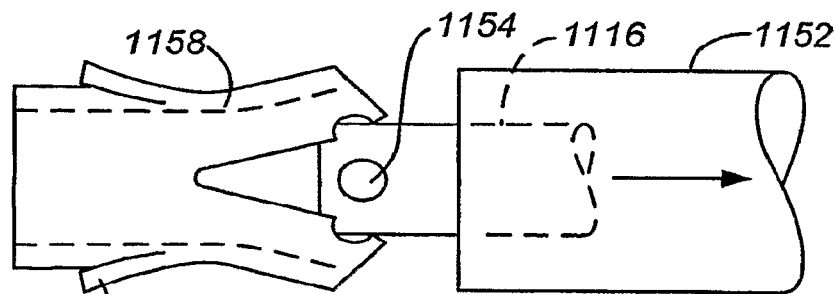
Figure 15D:
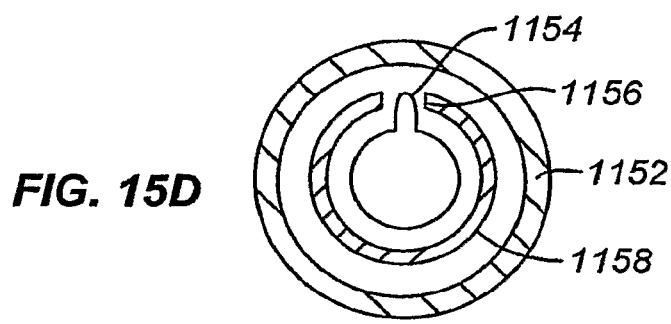

The component depicted in FIGS. 15A-C is a ratchet design used to hold the device in place until the delivery device, e.g. catheter, is decoupled. The device is configured to provide a ratchet mechanism having a ratchet wheel and pawl within the interior surface of the proximal end of the device. A retaining sheath 1152 is provided to hold the ratchet mechanism and prevent it from opening up. The sheath is retracted and then the pull wire 1116 is pulled out. Flanges or tabs 1142 are provided that extend away from a central axis when not constrained. A pin 1154 can be provided that slides within a slot 1156 in the tube 1755 and is engaged at a widened aperture 1156'. When withdrawing the pull wire 1116 the sides of the ratchet can deform away from the central axis A as shown in FIG. 15C to allow the pull wire to exit. The ratchet tube 1158 can be formed of shape memory material, such as nitinol which can heat set the ratchet to open once the sheath 1152 is removed. Alternatively, the ratchet tube can be formed from stainless steel. Use of stainless steel would require the pull wire with the peg to be pulled out. FIG. 15D is a cross-section taken along the lines D-D of FIG. 15A.

Figure 16A:
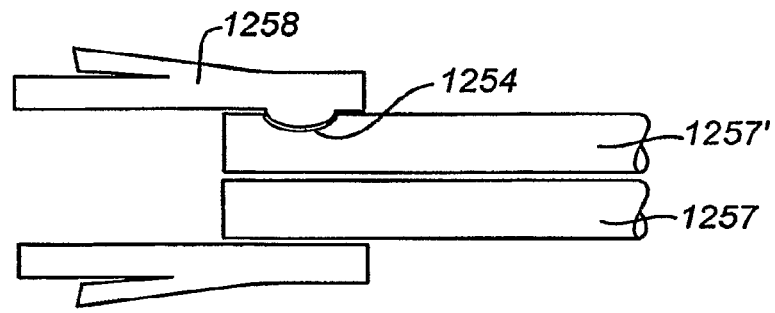
FIG. 16A-C illustrates a decoupling system.
Figure 16B:
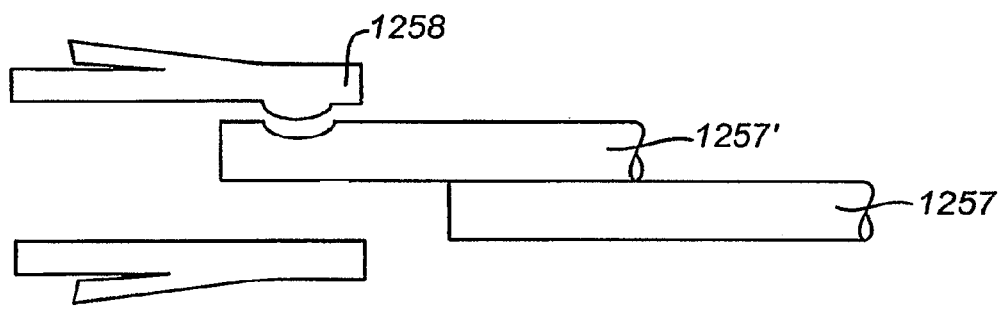
Figure 16C:
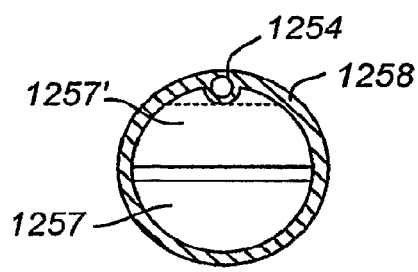

FIGS. 16A-C illustrate yet another mechanism suitable for use with the implantable devices of the invention, wherein a detent 1254 positioned on the inner surface of the ratchet tube 1258. Two tubes 1257, 1257' are used to lock the device in place. Once the first tube 1257 is pulled out, the second tube 1257' can deflect away from the detent 1254, thereby unlocking the coupling. The detent 1254 can be configured in the shape of a ball as depicted in the cross-section shown in FIG. 16C. This system can be used to de-couple the delivery device.

Figure 17A:
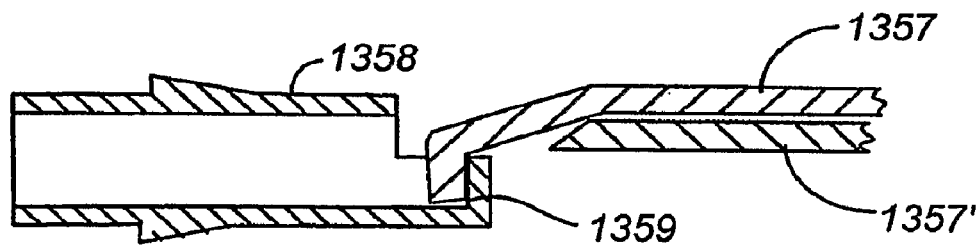
FIGS. 17A-B depict a mechanism for decoupling the delivery device from a lung volume reduction device.
Figure 17B:
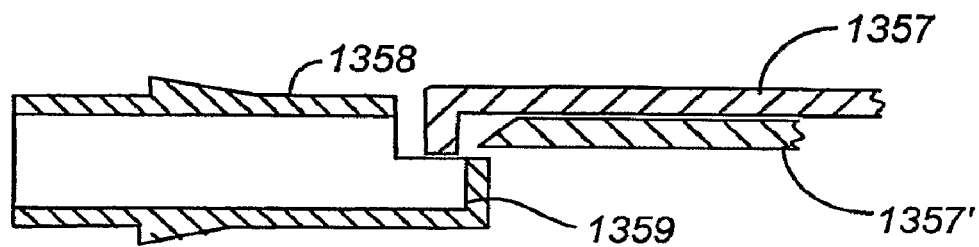
Figure 18:
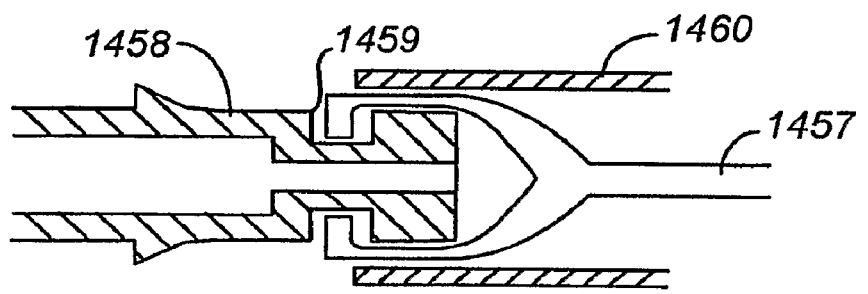
FIG. 18 illustrates another mechanism suitable for use in decoupling the delivery device from a lung volume reduction device.
Figure 19A:
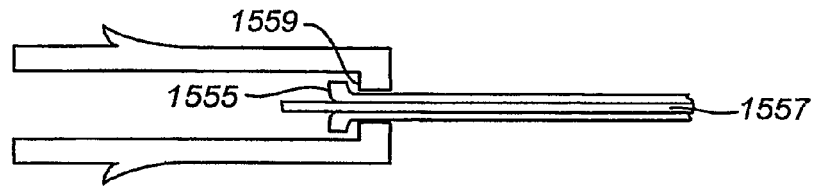
FIGS. 19A-B illustrate yet another embodiment of a decoupling system.
Figure 19B:
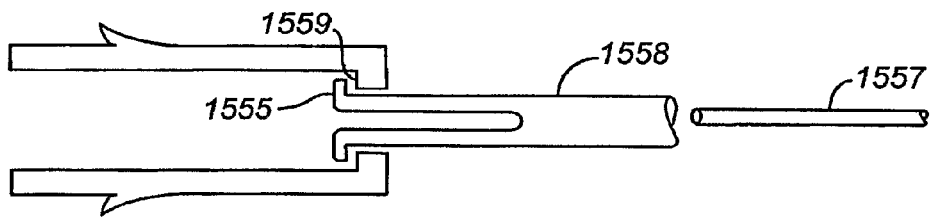
Figure 20A:
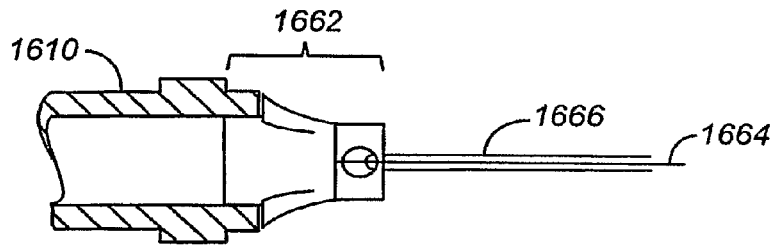
FIGS. 20A-E illustrate a hitch pin configuration useful in decoupling the delivery device.
Figure 20B:
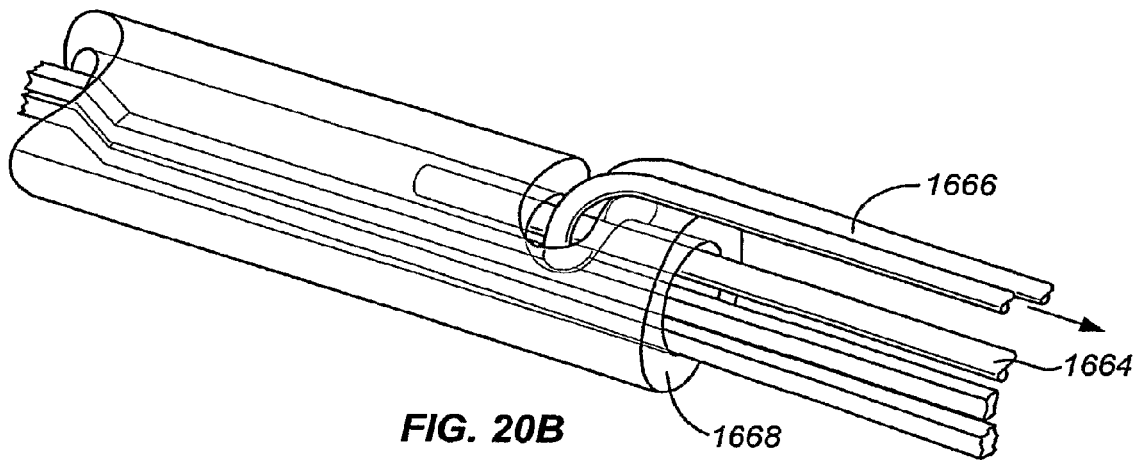
Figure 20C:
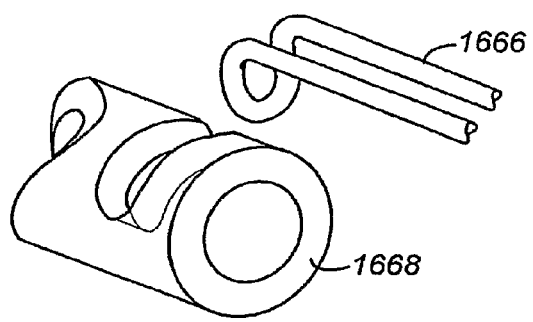
Figure 20D:
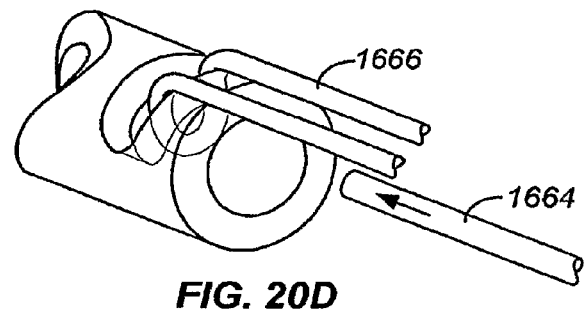
Figure 20E:
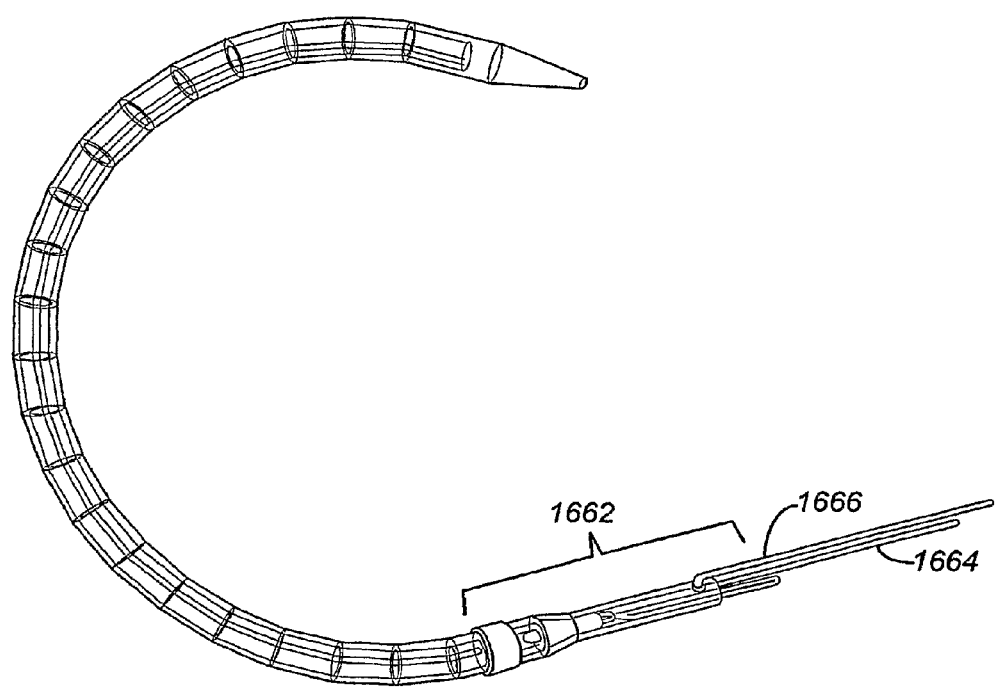

FIGS. 17A-B and 18 depict alternative mechanisms for de-coupling the delivery device. As depicted in FIGS. 17A-B, a push bar 1357' is used to push back a latch bar 1357. The latch bar is adapted to engage a lip on the interior of the device, the push bar deflects the latch bar away from the lip 1359 and enables the bar to be withdrawn as shown in FIG. 17B. In FIG. 18, a retaining sheath 1460 is employed which, when withdrawn in the proximal direction, enables the arms of the latch device 1458 to deflect away from a central axis A7 and disengage from a retaining lip 1459. FIGS. 19A-B illustrates yet another embodiment. In the embodiment illustrated, a central pin 1557 is withdrawn which allows the claws 1555 to relax and withdraw away (toward a central axis) from retaining lip 1559 of latch bar 1558.

FIGS. 20A-E illustrates a hitch pin configuration useful for use in actuating and de-coupling the delivery device. A portion of the lung volume reduction device 1610 is depicted with an actuation element 1616 positioned therein. A locking mechanism 1640 such as depicted in FIG. 14 engages the proximal end of the device 1610. A hitch pin de-coupling system 1662 is attached to the locking mechanism 1640. Alternatively, the hitch pin can be adapted to decouple from the ratchet mechanism. The hitch pin system 1662 has a hitch pin wire 1664 that engages a hitch pin 1666 loop wire. When the hitch pin wire is inserted it maintains the hitch pin in contact with the locking shaft 1668.

Figure 21:
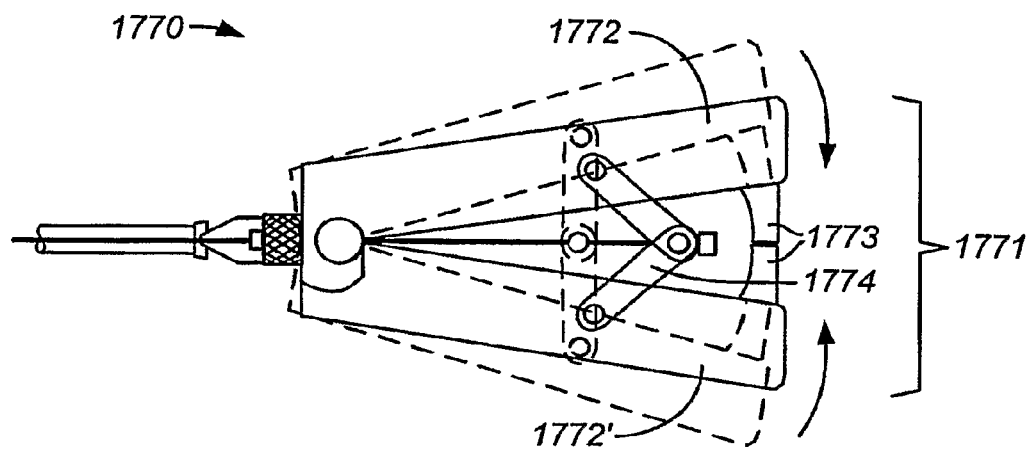
FIG. 21 illustrates an activation mechanism suitable for use with the devices of the invention.
Figure 22:
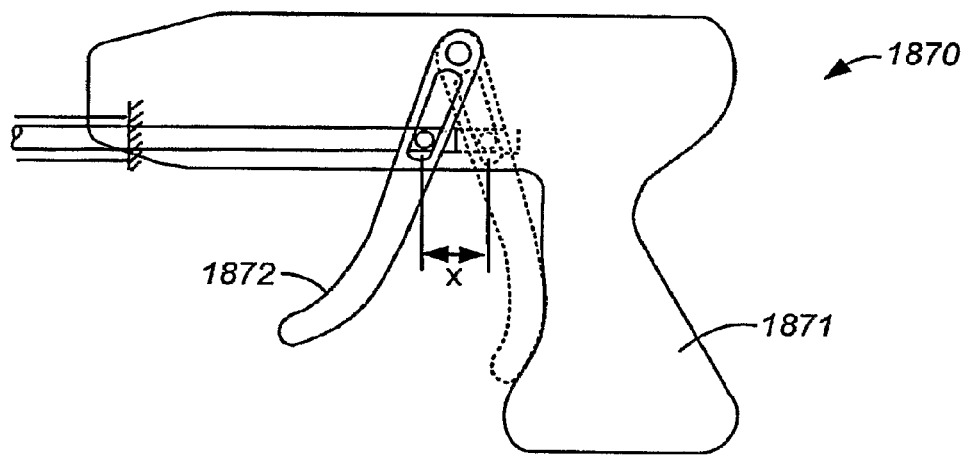
FIG. 22 illustrates an alternative mechanism for proximally controlling the deployment of the device.
Figure 23:
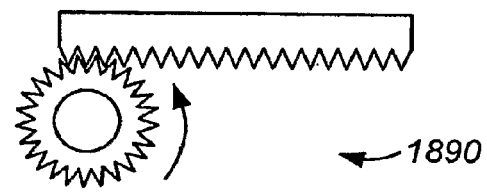
FIG. 23 illustrates a spur gear suitable for use with control mechanisms of the invention.

FIG. 21 illustrates an activation mechanism suitable for use with the invention. The activation mechanism 1770 has a handle 1771 which a user can squeeze to activate the device. Two levers 1772, 1772' of the handle will be advanced toward each other as the user squeezes the levers together. Stoppers 1773 can be provided to control or pre-set the amount of pulling the activation mechanism can achieve in a single squeeze. The amount of displacement of wire at the distal end is indicated by the displacement x from a vertical axis that occurs of hinged lever 1774 positioned between the two levers of the activation mechanism when the user squeezes the levers together. FIG. 22 illustrates an alternative mechanism for proximally controlling the deployment of the device. As illustrated in FIG. 22 a pistol actuator 1870 is provided that has a trigger 1872 which can be pulled back toward a handle 1871. The amount of displacement of the wire can be controlled by the distance x that the trigger is pulled toward the handle. A linear actuation motion can also be simulated by using spur gears 1890 having teeth machined parallel to its axis, such as that shown in FIG. 23.

Figure 24:
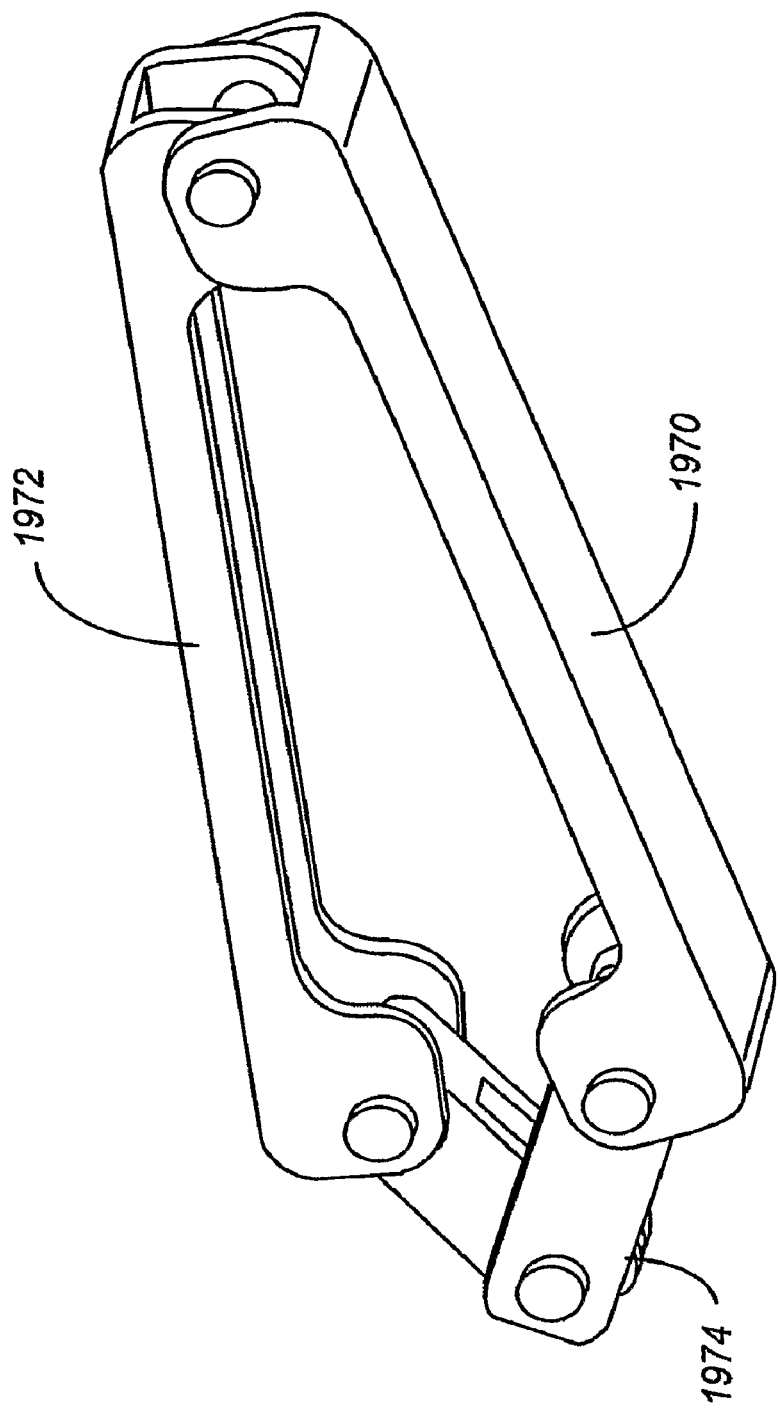
FIG. 24 illustrates a proximal control device for actuating an implant.

FIG. 24 illustrates another proximal control mechanism 1970 adapted for user control of the delivery device and implant. The control mechanism includes a hand grasper 1972, 1972' with four-bar linkages 1974. When a user presses down on the hand grasper, the device adapts its configuration from angled to flat, which pulls the catheter proximally (toward the user) to actuate the implant within the patient.

Figure 25:
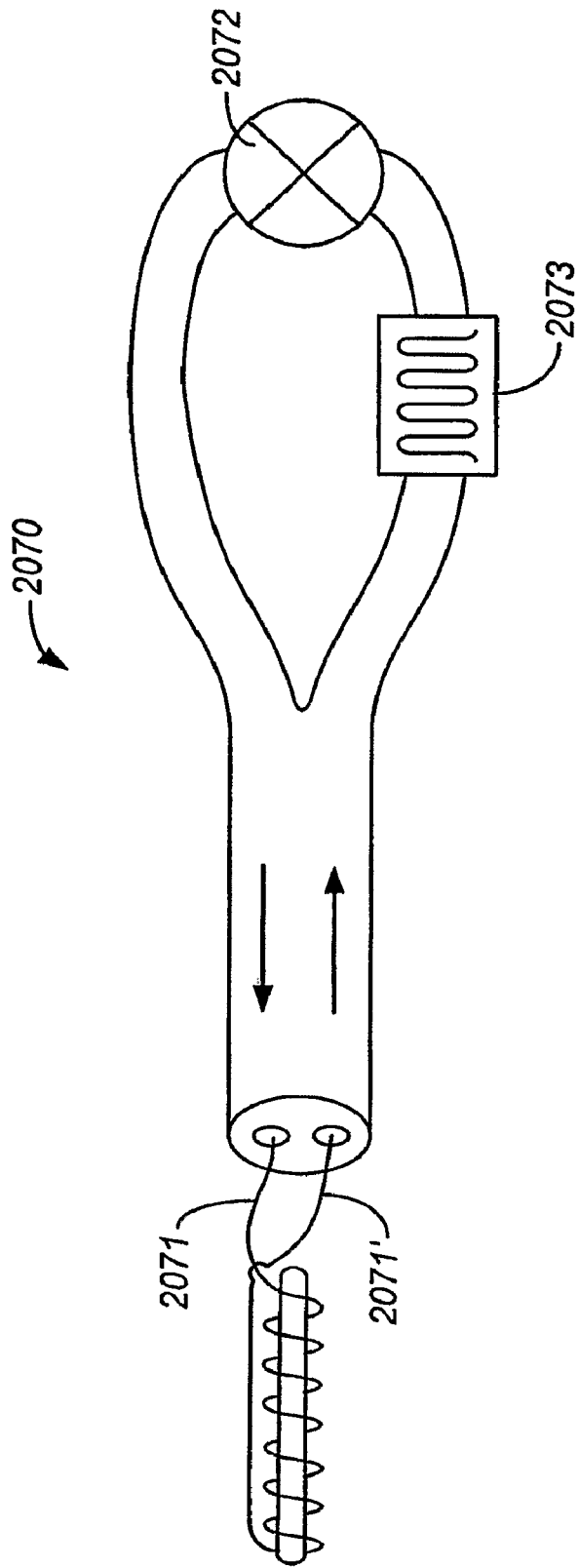
FIG. 25 illustrates another proximal control device and delivery catheter system for actuating an implant while maintaining a desired temperature at a distal end.

The device illustrated in FIG. 25 is another proximal control mechanism 2070 adapted for the user to control the temperature of a Nitinol self-recovering implant during the deployment process. In this embodiment, cold saline is advanced distally 2071 to maintain the Nitinol implant in a martensitic state (i.e., a state having a "soft" microstructure that allows deformation). A return path 2071' is provided to bring the saline back to the mechanism for cooling. Maintenance of the martensitic state enables the device to remain flexible and soft during implant delivery without modifying the implant's programmed shape. Chilled saline, liquid nitrogen, liquid $CO_2$ or other suitable materials that are colder than body temperature, can be pumped 2072 or circulated to the implant. A chiller 2073 can be provided to cool down the material circulating to the device on its return path. In some embodiments, it may be desirable to control the temperature of the device, e.g., during the implantation process with a distal temperature sensor and feedback that may be transmitted via electric signal on a wire or electro-magnetic waves in a wireless fashion.

Figure 26:
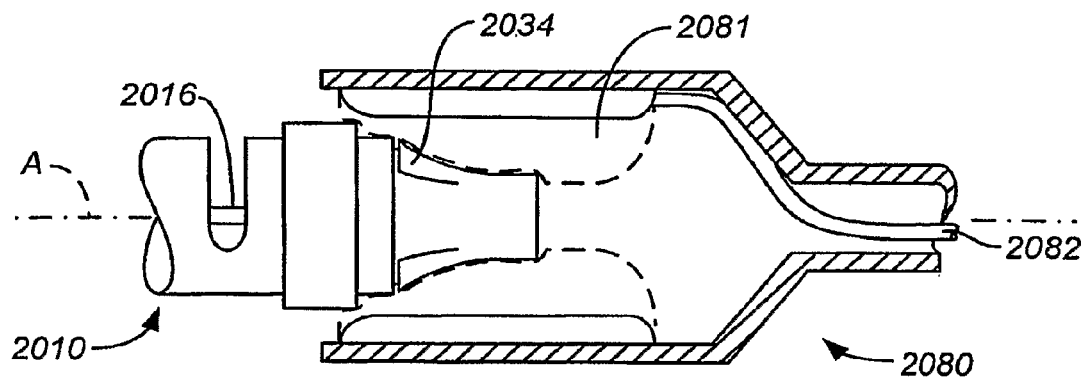
FIG. 26 illustrates yet another proximal control device for use in recapture of an implanted device.
Figure 27A:
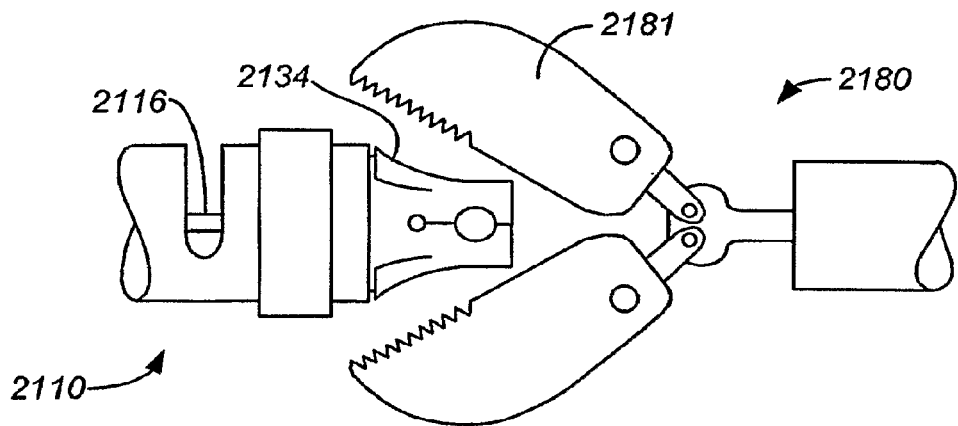
FIGS. 27A-B illustrates an alternative embodiment of a retrieval device.
Figure 27B:
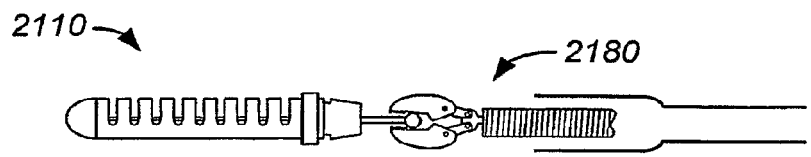

Turning now to FIG. 26, a distal configuration of a recapture device 2080 is depicted. The proximal end of the implanted device 2010 is engaged by the recapture device 2080 which is adapted to encircle the exterior of the implanted device. The device comprises a high pressure balloon 2081 adapted to engage a recovery catheter. An inflation port 2082 is provided through which, for example, cold fluid can be pumped to facilitate deflecting the nitinol tabs 2034. Once the tabs are deflected and moved toward the central axis A of the device, the lock mechanism holding the actuation wire in a curved condition can be released, the implanted device straightened and withdrawn. FIGS. 27A-B illustrates an alternative embodiment of a retrieval device 2180, where forceps are used to provide lateral force on the tabs, thus pressing the tabs in toward the central axis of the device to enable the lock mechanism holding the actuation wire to be released as described above. As illustrated in FIG. 27B, the forceps can then withdrawn the straightened device by pulling on the device.

Figure 28A:
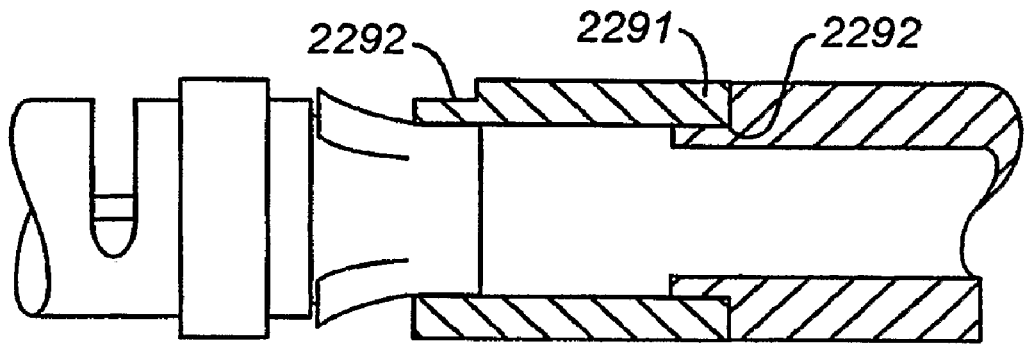
FIGS. 28A-B illustrate device components adapted to engage each other.
Figure 28B:
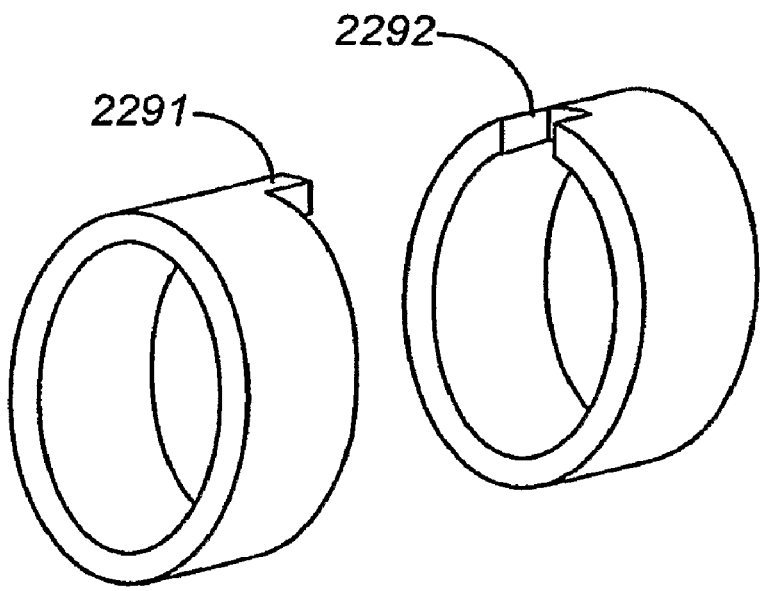

A variety of mechanisms can be used to couple the clip of the device to the catheter. As shown in FIGS. 28A-B, the implantable device 2210 has a ring with a key 2291 associated with one of the device or the delivery catheter and a keyway 2292 associated with an opposing ring associated with remaining one of the device or delivery catheter. As will be appreciated by those skilled in the art, more than one key or keyway can be provided, as desired, to control the torque. As shown in FIG. 28B, the two rings are adapted to abut each other to lock the device and allow transfer for torque between the catheter and the device. The key: keyway design illustrated in FIG. 28B can also be applied to the delivery or retrieval of devices and to the proximal end of the device.

Figure 29A:
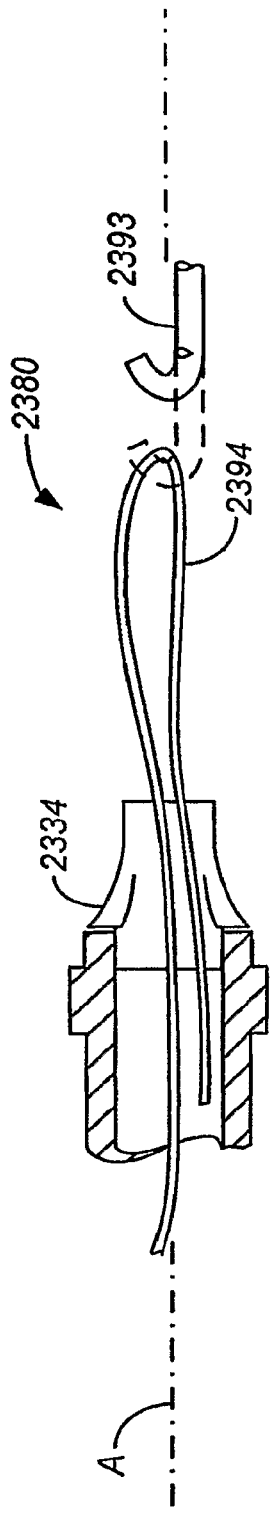
FIGS. 29A-C illustrate another retrieval mechanism.
Figure 29B:
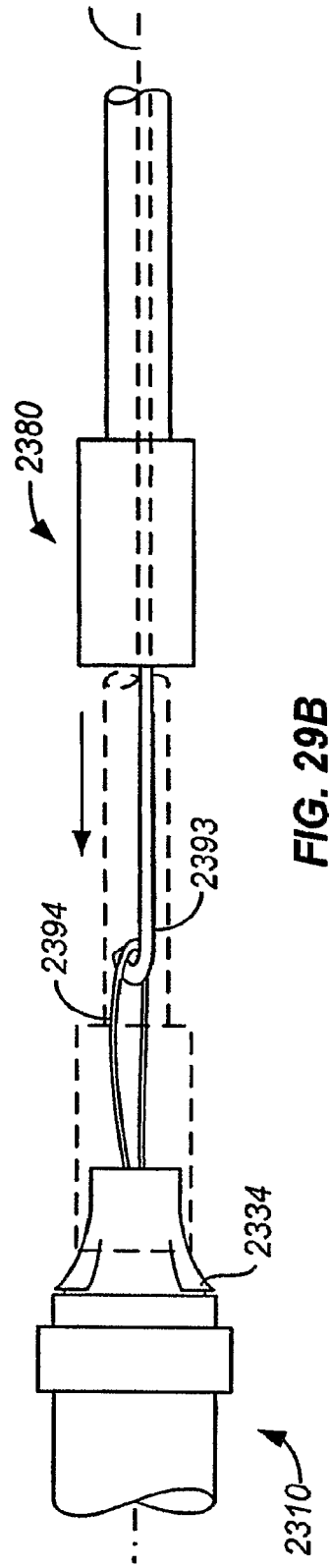
Figure 29C:
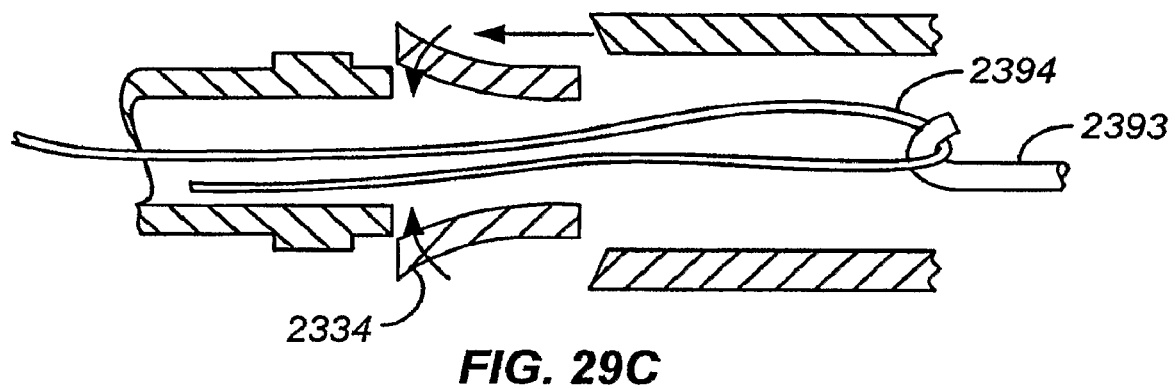
Figure 30A:
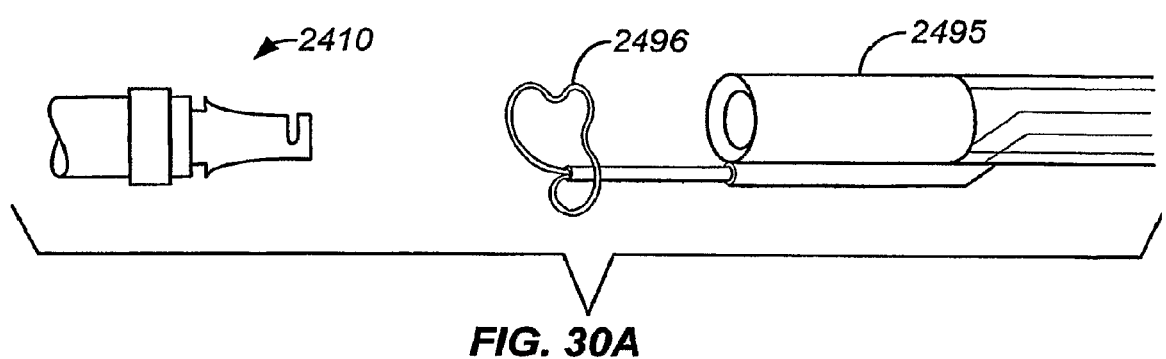
FIGS. 30A-B illustrate a retrieval device comprising a snare wire.
Figure 30B:
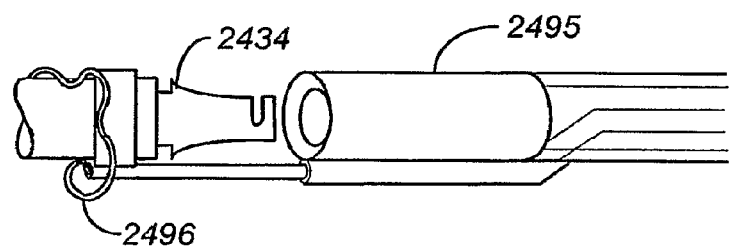

FIGS. 29A-C illustrates another retrieval mechanism 2380. The retrieval mechanism employs a hook 2393 adapted to hook into a loop 2394 at the proximal end of the device. The hook can be incorporated into the actuation mechanism 2316 such that hook 2393 extends from the actuation mechanism at the proximal end of the device 2310. Once hooked the apparatus de-activates the locking mechanism, which releases the tension on the actuator 2316. The catheter is then advanced to engage the locking flanges 2334 to push them in toward a central axis A, unlocking the device 2310 by removing tension from the actuation member 2316 and allowing the device to be withdrawn or relocated. In yet another embodiment illustrated in FIGS. 30A-B, a hypotube 2495 associated with, for example, a catheter is adapted to slide over the proximal end of the device 2410. A snare wire 2496 is configured to fit over the proximal end of the device much like a lasso. In operation, the snare wire 2496 is looped over the proximal end of the device 2410, and pulled proximally to push the hypo tube distally toward the device. This enables the combination to hold onto the implant, advance the locking hypo tube forward to unlock the tabs or flanges 2434.

Figure 31A:
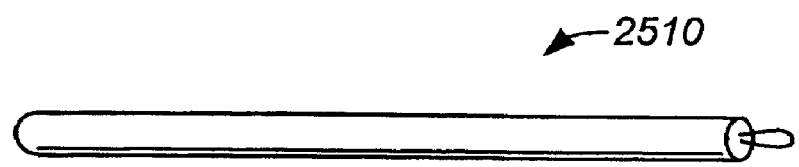
FIGS. 31A-D illustrates devices in a variety of deployed conditions.
Figure 31B:
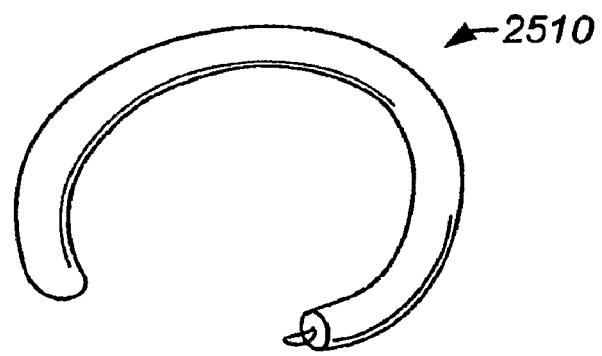
Figure 31C:
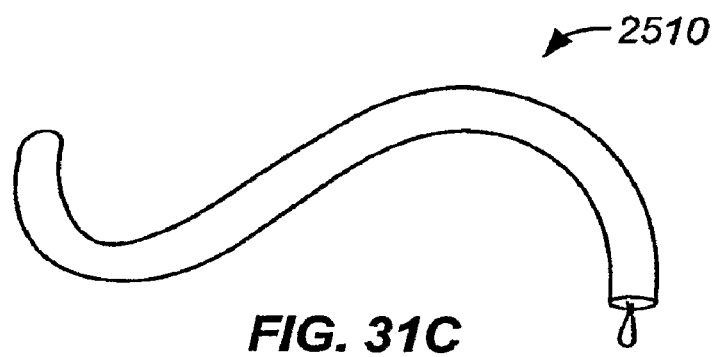
Figure 31D:
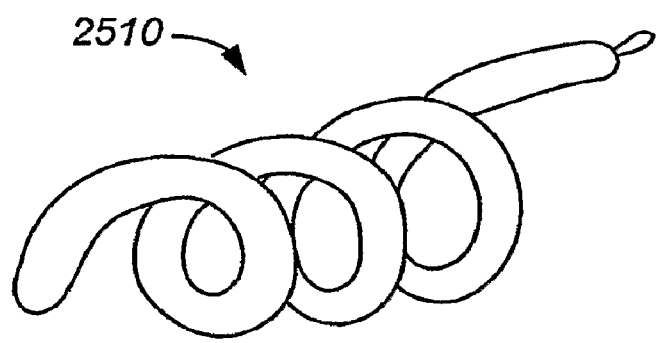

FIGS. 31A-D illustrates devices 2510 according to the invention in a variety of deployed configurations. FIG. 31A illustrates the device 25/0 having a longitudinal configuration, such as the configuration assumed prior to deployment. When the device is implanted and placed in compression or tension axially, the device will preferentially bend. The actual preferential bending will vary depending upon the configuration of the device. For example, the location, depth, and orientation of the slots depicted in FIGS. 4-8; or the orientation of the walls of the segments of FIG. 9. As FIG. 31B illustrates, for example, where the device 2510 has evenly spaced c-cuts or notches along its length the device will preferentially bend such that the walls of forming the "c" or notch will approach each other, or pinch together, resulting in a deployed device that has preferentially bent into a curved "c" shape (see, FIGS. 4-5). This results because as tension is applied on the actuation device, or wire, the implant deforms and the wire takes a shorter path. FIG. 31C illustrates a device deployed into an "S" shape, such as would be achieved using a configuration like that depicted in FIG. 6. As will be appreciated, the S-shape could continue, much like a sine wave, in an many curves as desired depending upon the configuration of the device. FIG. 31D illustrates a device deployed into a spiral configuration (see, FIG. 7). As will be appreciated by those skilled in the art upon reviewing this disclosure, other configurations can be achieved by, for example, altering the size and location of the c-cuts on the tubular member, or by altering the configuration of the segments illustrated in FIGS. 9-10. Once the device preferentially bends, the device imparts a bending force on the lung tissue which results in a reduction of lung volume. As is appreciated, from the configurations shown in FIG. 31 the implant, once re-shaped, is shorter in length than the deliverable implant configuration. The shortening occurs when for example, the distance between the proximal end and the distal end is reduced. Typically, the deliverable shape of the device is such that it fits within a cylindrical space that is 18 mm in diameter or smaller. Thus, the implant can come into contact with tissue that is larger than $10^{-6}$ square inches per linear inch of the implant length. The re-shaped or deployed implant can be configured in a variety of shapes to lie within a single plane, or to adopt any other suitable configuration, such that it does not lie within a single plane. Additionally, the device can have varying rates of curvature along its length.

Figure 32:
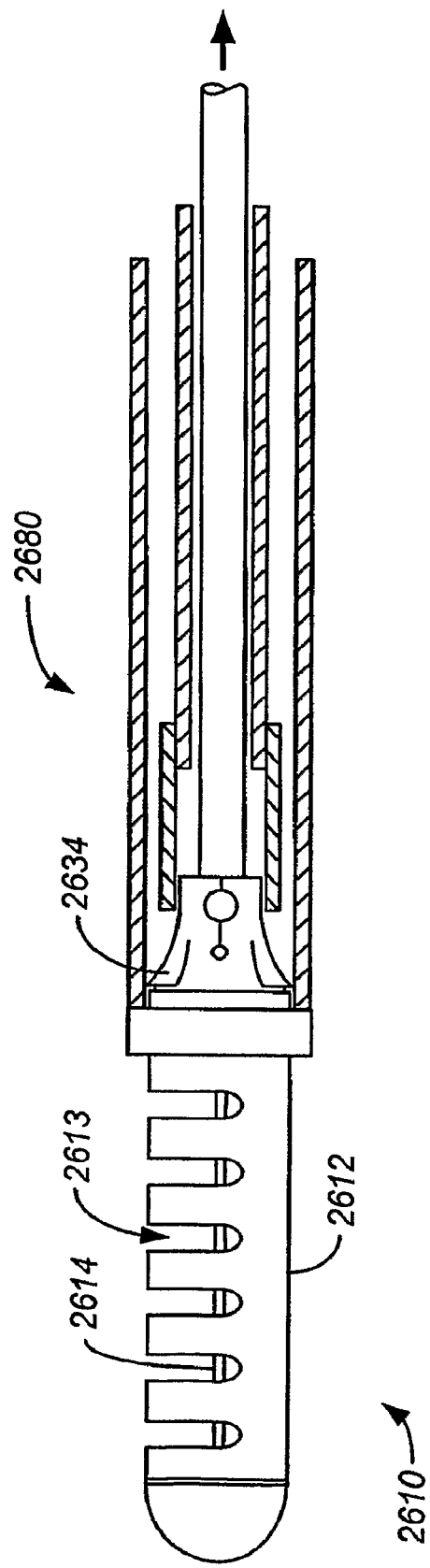
FIG. 32 illustrates a lung volume reduction device in combination with a delivery catheter.

FIG. 32 illustrates a lung volume reduction device 2610 in combination with a delivery device 2680. The device 2610 is adapted to provide a tubular member 2612 having a lumen 2613 through which an actuation element 2614 is provided. The tubular member 2612 has a series of c-cuts 2614 along its length that enable the device to preferentially bend when deployed. As will be appreciated, for purposes of illustration, a device similar to that depicted in FIG. 4 has been illustrated. Other devices can be used without departing from the scope of the invention. A device 2680 is provided that engages flanges 2634 of a lock mechanism to push the flanges in toward a central axis enabling tension applied to the actuation element 2614 to be relieved, thus enabling the device to be removed. The device can be activated by pulling the central rod in a proximal direction. The decoupler (outer rod) is then pulled in the proximal direction.

Figure 33A:
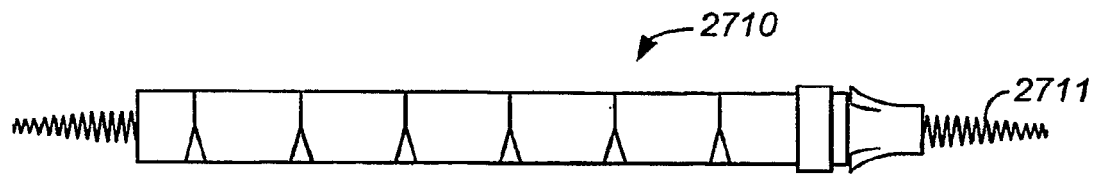
FIGS. 33A-C illustrate a variety of device configurations with atraumatic tips.
Figure 33B:
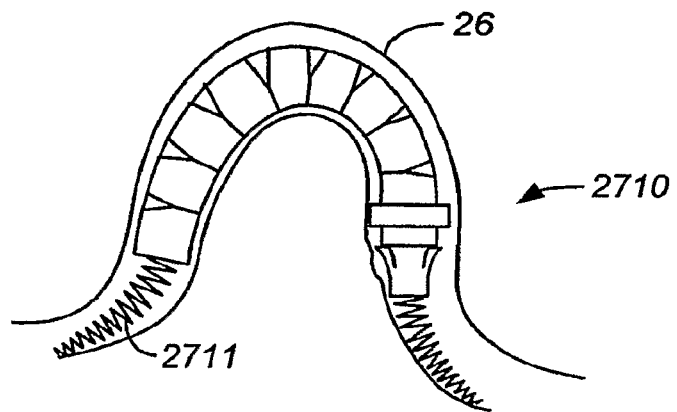
Figure 33C:
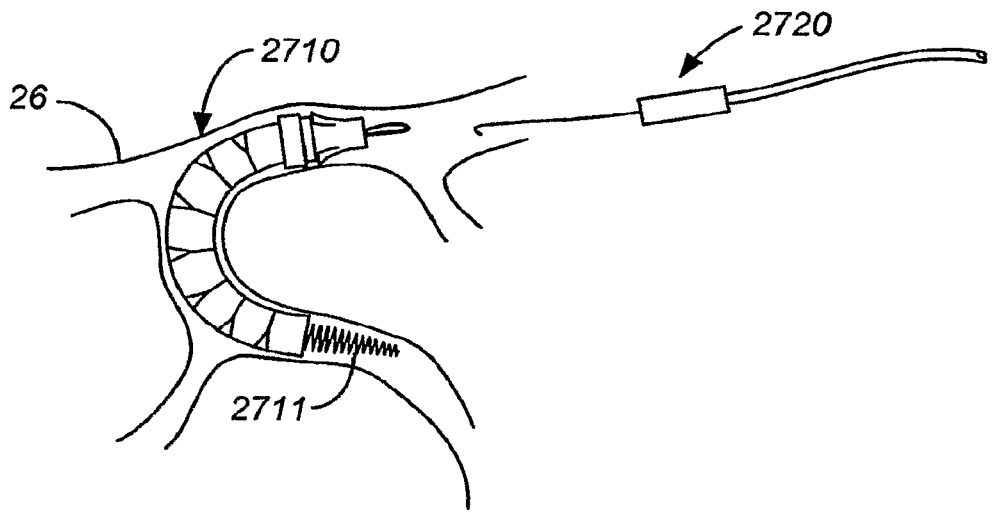

FIGS. 33A-C illustrates devices 2710 according to the invention implanted within, for example, a bronchiole 26. The device 2710 depicted in FIG. 33A is configured to provide an atraumatic tip 2711 on either end of the device. When the device 2710 is activated within the bronchiole 26 the device curves and imparts a bending force on the lung tissue. As a result of the bending pressure, the tissue curves and compresses upon its self to reduce lung volume. Additionally, deployment of the device can result in the airway becoming bent. As illustrated in FIG. 33C the device can also be configured with a single atraumatic tip so that the deployment mechanism 2720 can easily interface with the proximal end of the device.

Figure 34A:
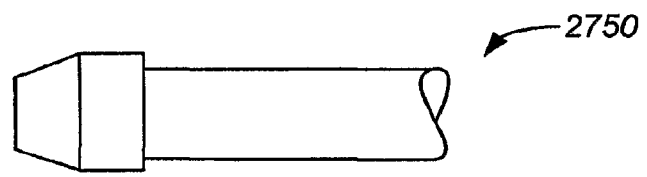
FIGS. 34A-B illustrate a withdrawal system having a blade to separate the device from the surrounding tissue.
Figure 34B:
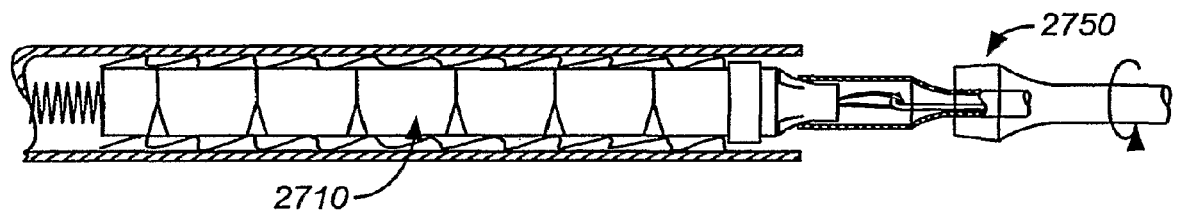

In some instances, where the device has been implanted for a length of time sufficient for tissue in-growth to occur, a torquable catheter 2750 having a sharp blade (not shown) within its lumen can be advanced along the length of the device 2710 to enable tissue to be cut away from the implant prior to withdrawal such as shown in FIGS. 34A-B. This enables the device to be cut away from the airway wall in order to facilitate withdrawal.

Figure 35A:
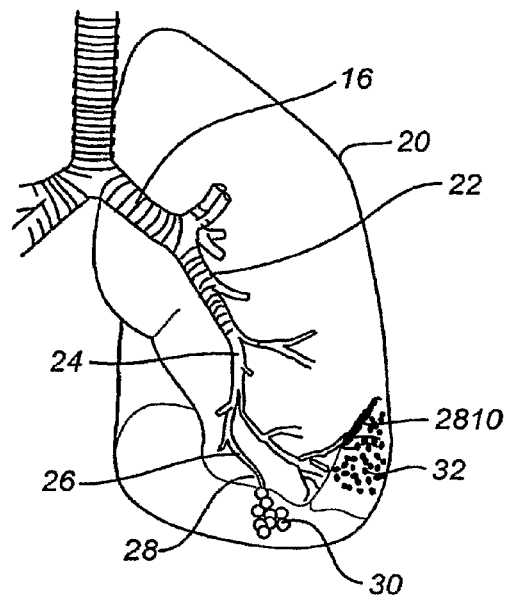
FIGS. 35A-C illustrate a device implanted within the lungs.
Figure 35B:
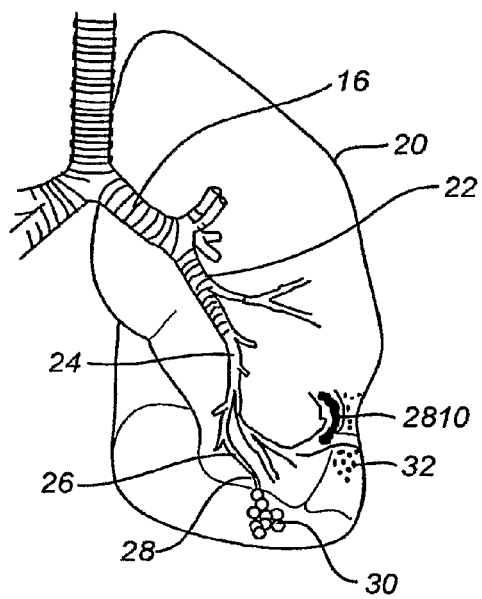
Figure 35C:
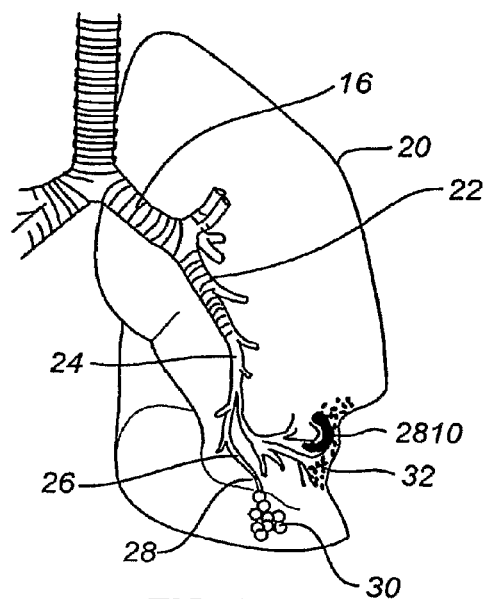

FIG. 35A-C illustrates the process of implanting the device within a lung. As is evidence, the device 2810 is advanced is a configuration where the device adapts to the anatomy of the lungs through the airways and into, for example, the bronchioles until it reaches a desired location relative to the damaged tissue 32. The device is then activated by engaging the actuation device, causing the device to curve and pull the lung tissue toward the activated device (see, FIG. 35B). The device continues to be activated until the lung tissue is withdrawn a desired amount, such as depicted in FIG. 35C. As will be appreciated by those skilled in the art, withdrawing the tissue can be achieved by, for example, curving and compressing a target section of lung tissue upon deployment of one of the configurable devices disclosed herein. Once activated sufficiently, the deployment device is withdrawn from the lung cavity.

Figure 36A:
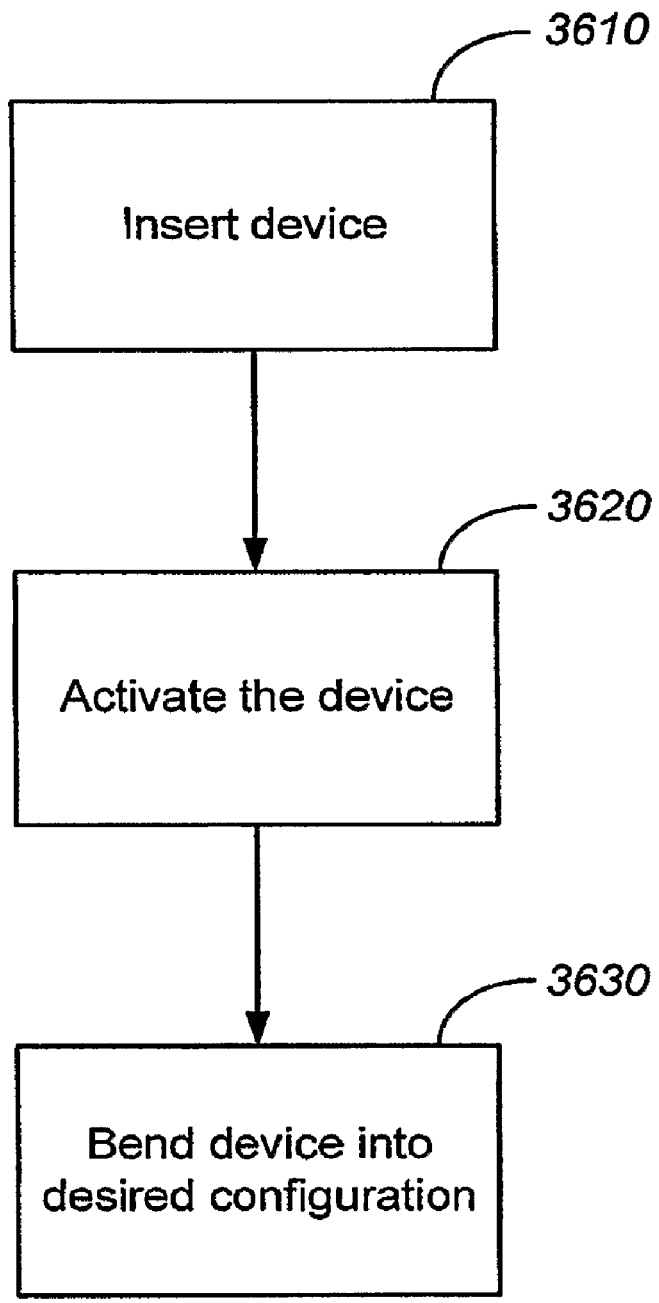
FIG. 36A illustrates a method steps for implanting the device.

A variety of steps for performing a method according to the invention would be appreciated by those skilled in the art upon review of this disclosure. However, for purposes of illustration, FIG. 36A illustrates the steps including, insertion of the device 3610, activating the device 3620, such as by activating an actuator; bending the device into a desired configuration 3630 and locking the device into a deployed condition. As will be appreciated the step of bending the device can be achieved by activating the actuator, as described above, or by the implant being restored into a preconfigured shape.

In one embodiment, the device operation includes the step of inserting a bronchoscope into a patient's lungs and then inserting an intra-bronchial device or lung volume reduction device into the bronchoscope. The intra-bronchial device is then allowed to exit the distal end of the bronchoscope where it is pushed into the airway. A variety of methods can then be used to verify the positioning of the device to determine if the device is in the desired location. Suitable methods of verification include, for example, visualization via visualization equipment, such as fluoroscopy, CT scanning, etc. Thereafter the device is activated by pulling the pull wire proximally (i.e., toward the user and toward the exterior of the patient's body). At this point, another visual check can be made to determine whether the device has been positioned and deployed desirably. Thereafter, the device can be fully actuated and the ratchet can be allowed to lock and hold the device in place. Thereafter, the implant is decoupled from the delivery catheter and the delivery catheter is removed.

Figure 36B:
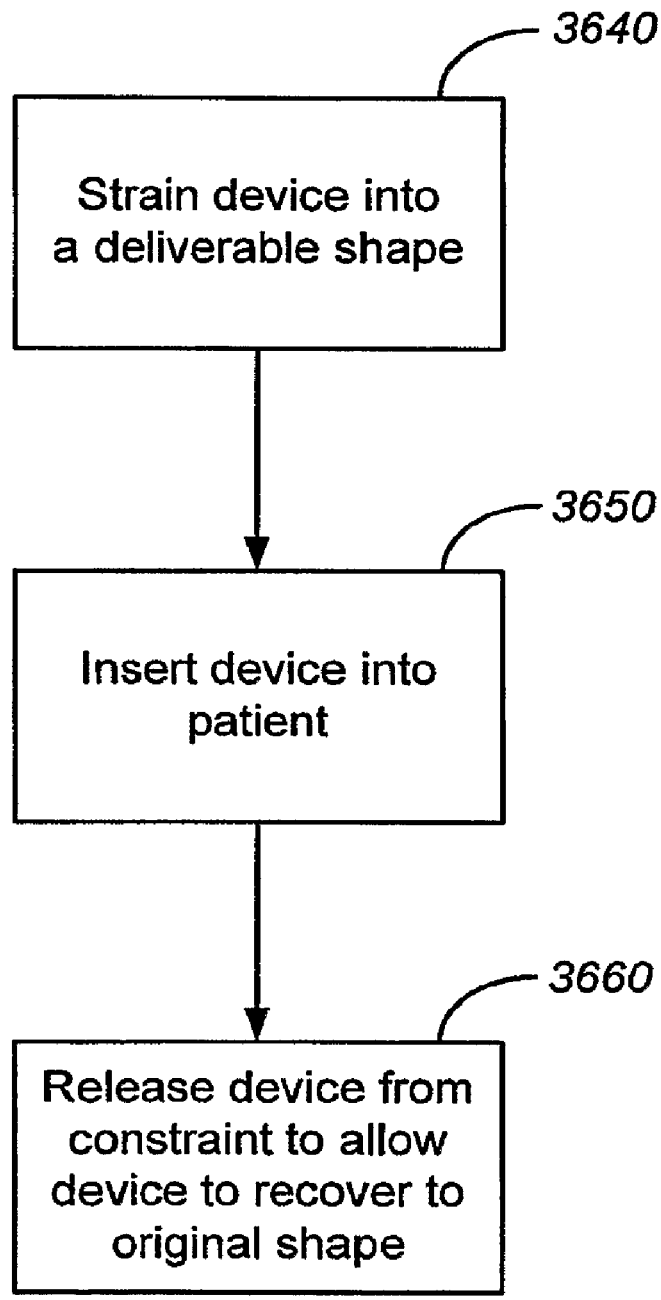
FIG. 36B illustrates a method steps for implanting the device.

Another method of tensioning the lung is shown in FIG. 36B which illustrates steps that include, applying bending loads or force to strain a device from a first shape into a deliverable shape without plastically or permanently bending the device 3640, delivering the device into the patient using the bronchoscope or other delivery system components to hold the device in a deliverable shape while it is being introduced 3650 and then removing the constraint used to hold the device to allow it to recover back to it's first shape 3660. Elastic recovery of the device will drive the device to a more bent condition that will apply force to nearby lung tissue. The bending forces locally compress tissue near the implant and apply tension on lung tissue in surrounding regions to restore lung recoil and enhance breathing efficiency. The first shape is adapted to be elastically constrained by a delivery device to a deliverable configuration whereby removal of the delivery device allows the implant to recoil and be reshaped closer to its first shape.

Figure 37:
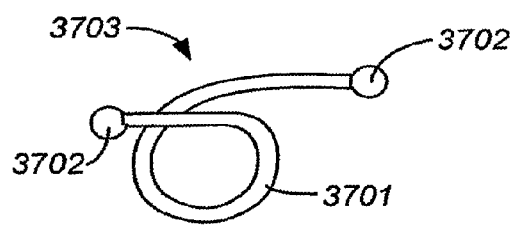
FIG. 37 illustrates a device configuration.

FIG. 37 shows an example of an implantable device 3703 made from Nitinol metal wire 3701. Nickel-Titanium, Titanium, stainless steel or other biocompatible metals with memory shape properties or materials with capabilities to recover after being strained 1% or more may be used to make such an implant. Additionally, plastics, carbon based composites or a combination of these materials would be suitable. The device is shaped like a French horn and can generally lie in a single plane. The ends are formed into a shape that maximizes surface area shown in the form of balls 3702 to minimize scraping or gouging lung tissue. The balls may be made by melting back a portion of the wire, however, they may be additional components that are welded, pressed or glued onto the ends of wire 3701.

A Nitinol metallic implant, such as the one illustrated in FIG. 37, may be configured to be elastic to recover to a desired shape in the body as any other type of spring would or it can be made in a configuration that may be thermally actuated to recover to a desired shape. Nitinol can be cooled to a martensite phase or warmed to an austenite phase. In the austenite phase, the metal recovers to its programmed shape. The temperature at which the metal has fully converted to an austenite phase is known as the Af temperature (austenite final). If the metal is tuned so that the Af temperature is at body temperature or lower than body temperature, the material is considered to be elastic in the body and it will perform as a simple spring. The device can be cooled to induce a martensite phase in the metal that will make the device flexible and very easy to deliver. As the device is allowed to heat, typically due to body heat, the device will naturally recover its shape because the metal is making a transition back to an austenite phase. If the device is strained to fit through a delivery system, it may be strained enough to induce a martensite phase also. This transformation can take place with as little as 0.1% strain. A device that is strain induced into a martensite phase will still recover to its original shape, and convert back to austenite after the constraints are removed. If the device is configured with an Af temperature that is above body temperature, the device may be heated to convert it to austenite and thermally activate its shape recovery inside the body. All of these configurations will work well to actuate the device in the patient's lung tissue. The human body temperature is considered to be 37 degrees C. in the typical human body.

Figure 38:
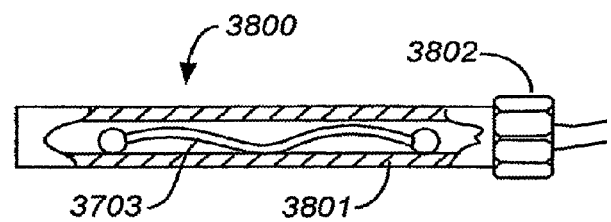
FIG. 38 illustrates a device in a loading cartridge.

FIG. 38 illustrates a cutaway view of a delivery cartridge system 3800 that constrains the implant device 3703 in a deliverable shape. The device 3801 may be shipped to the intended user in such a system or it may be used as a tool to more easily load the implant into a desired shape before being installed into the patient, bronchoscope or a catheter delivery device. The cartridge may be sealed or terminated with open, ends or one or more hubs such as the Luer lock hub 3802 that is shown. The implant should be constrained to a diameter that is the same or less than 18 mm diameter because anything larger than that will be difficult to advance past the vocal cord opening.

Figure 39:
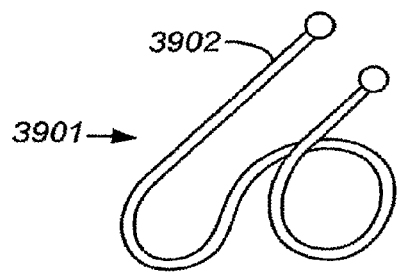
FIG. 39 illustrates a long device configuration.

FIG. 39 Illustrates another implant device 3901 that is shaped in a three dimensional shape similar to the seam of a baseball. The wire is shaped so that proximal end 3902 extends somewhat straight and slightly longer than the other end. This proximal end will be the end closest to the user and the straight section will make recapture easier. If it were bent, it may be driven into the tissue making it hard to access.

Figure 40:
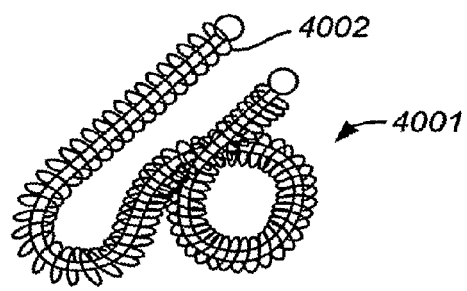
FIG. 40 illustrates a device configuration with a wire support frame.

FIG. 40 is an illustration of another implant system 4001, It is similar to that shown in FIG. 39 with the addition of a wire frame 4002 surrounding the device. The wire frame may be used, for example, to increase the bearing area that is applied to the lung tissue. By increasing the bearing area, the pressure born by the tissue is reduced along with a reduction in the propensity for the device to grow through lung structures or cause inflammatory issues. Small wires that apply loads in the body tend to migrate so we believe that the device should be configured to posses more than 0.000001 ($1^{-6}$ in$^2$) square inches of surface area per linear inch of the length of the device. The frame is one of many ways to provide a larger surface area to bear on the tissue.

Figure 41:
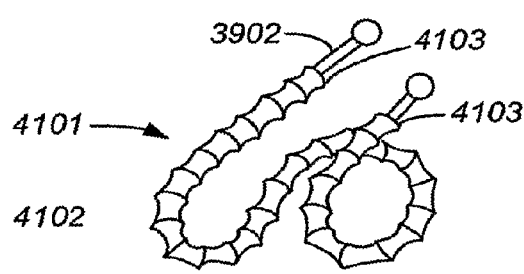
FIG. 41 illustrates a device configuration with a covering.

FIG. 41 shows yet another example of a device 4101 according to the invention. The device 4101 features a covering to increase bearing area 4102. In this example, the main wire 3902 is covered by a wire frame and a polymeric covering 4102. The covering may be made of any biocompatible plastic, thermoplastic, fluoropolymer, Teflon®, urethane, metal mesh, coating, silicone or other resilient material that will reduce the bearing pressure on the lung tissue. The ends of the covering 4103 may remain sealed or open as shown to allow the user to flush antibiotics into and out of the covering.

Figure 42:
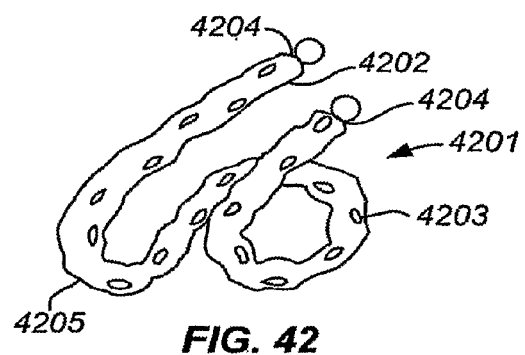
FIG. 42 illustrates a device configuration with a perforated covering.

FIG. 42 illustrates another configuration of the implant device 4201 showing a covering 4205 with perforations 4203 adapted and configured to allow the device to be flushed. The ends 4202 of the covering are sealed to the ends of the device to keep the two components fixed and prevent sliding of one or the other during deployment. The covering may be thermally bonded, glued or shrunk to a tight fit.

Figure 43:
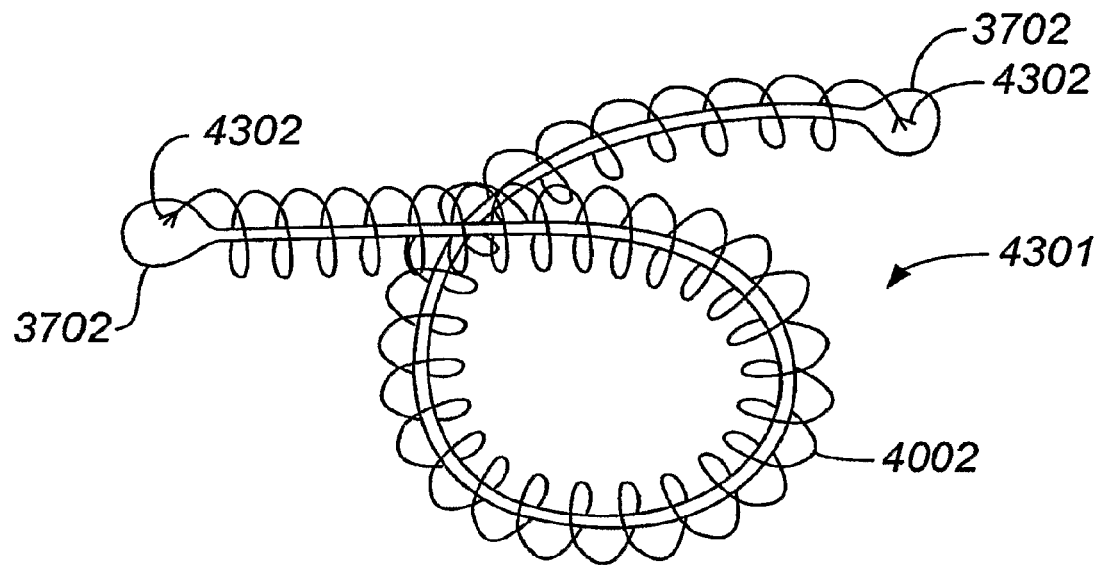
FIG. 43 illustrates a device configuration with an attached wire support frame.

FIG. 43 illustrates a device 4301 that has the wire frame 4002 joined to the ball ends 3702 at a junction 4302. The balls may be melted from the wire stock and the wire frame may be incorporated into the ball at that time. It may also be glued, pressed together, welded or mechanically locked together.

Figure 44:
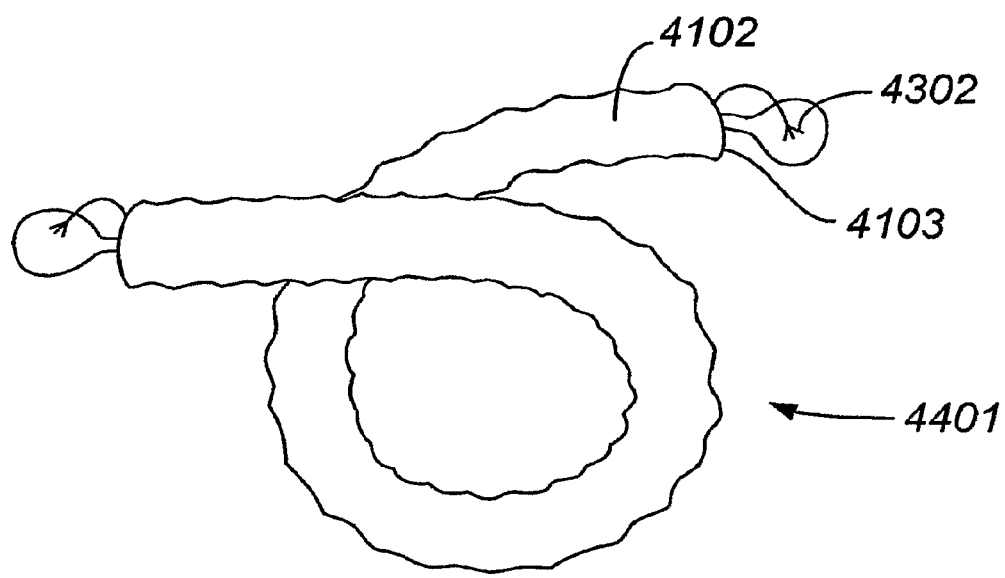
FIG. 44 illustrates a device configuration with an attached frame and covering.

FIG. 44 illustrates another implant device 4401 with an attached wire frame 4302, main wire 4103 and a covering 4102.

Figure 45:
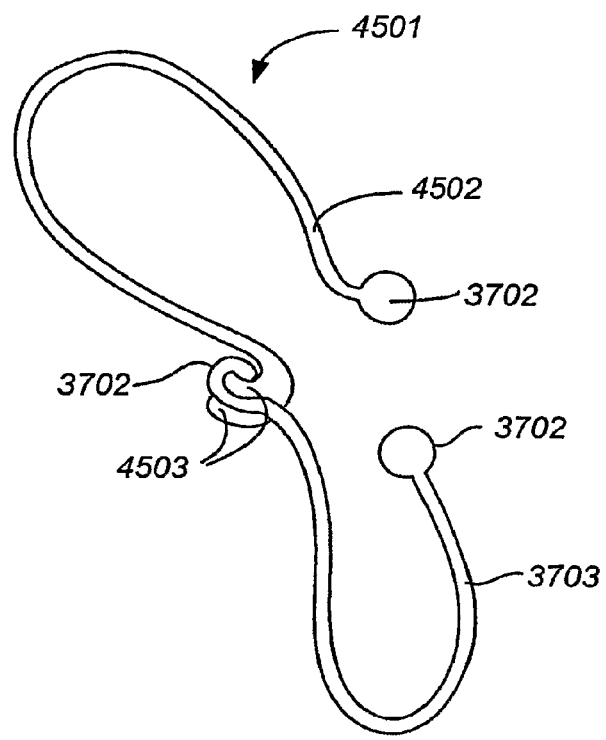
FIG. 45 illustrates a device configuration that is coupled to a second device.

FIG. 45 illustrates a system of one or more devices that can be hooked together 4501. The device 3703 is configured such that it terminates on both ends, for example, with blunt ball shaped ends 3702. The device 4502 is terminated on one end with an open cup and slot shape 4503 that allows the devices to be coupled together. These devices may be delivered together or coupled in-situ. Devices may be installed into a single duct in the lung or in different locations that may be linked together.

Figure 46:
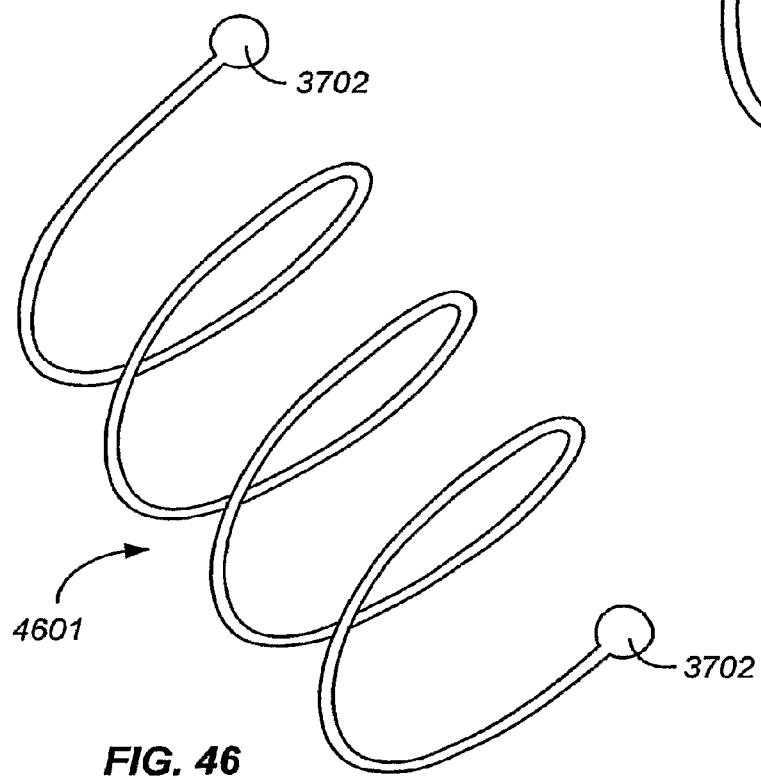
FIG. 46 illustrates a device configuration in a coil shape.

FIG. 46 illustrates another three dimensional device 4601 made in the form of a coil with ball terminations 3702.

FIGS. 47 and 48 illustrate how the device length is reduced when the device is deployed in-situ. The device shown in the delivery configuration 4802 in FIG. 47 is also shown in the deployed configuration 4803 in FIG. 48. The distance A between the device ends 3702 is large while the device is constrained by the constraining cartridge device 3801. Distance A is similar when the device is constrained by a loading cartridge, catheter or bronchoscope. FIG. 48 shows the same device in a deployed configuration 4803 in an airway 4801 that has been deformed by the shape recovery of the implant device. FIG. 48 shows that the distance B between the device ends 3702 is substantially shorter after the device is deployed.

As with, previous embodiments, the embodiments depicted in FIGS. 37-48 are adapted and configured to be delivered to a lung airway of a patient in a delivery configuration and to change to a deployed configuration to bend the lung airway. The devices are characterized in that the devices have a delivery configuration that is resiliently bendable into a plurality of shapes, such as the ones depicted in the Figures. The design of the devices can be such that strain relief is facilitated on both ends of the device. Further the ends of the device in either the delivery or deployed state are more resilient.

The devices can have any suitable length for treating target tissue. However, the length typically range from, for example, 2 cm to 10 cm, usually 5 cm. The diameter of the device can range from 1.00 mm to 3.0 mm, preferably 2.4 mm. The device is used with a catheter which has a working length of 60 cm to 200 cm, preferably 90 cm.

In operation the devices shown in FIGS. 37-48 are adapted and configured to be minimally invasive which facilitates easy use with a bronchoscope procedure. Typically, there is no incision, and no violation of the pleural space of the lung during deployment. Furthermore, collateral ventilation in the lung does not affect the effectiveness of the implanted device. As a result, the devices are suitable for use with either homogeneous and heterogeneous emphysema.

Each of the devices depicted in FIGS. 37-48 are adapted and configured to impart bending force on lung tissue. For example, a spring element can be provided, as illustrated in FIG. 40 that imparts bending force on lung tissue. The implantable spring element that can be constrained into a shape that can be delivered to a lung airway and unconstrained to allow the element to impart bending force on the airway to cause the airway to be bent.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37° Celsius or colder. Additionally, at least a portion of the metal of the device can be transformed to the martensite phase in the delivery configuration and/or can be in an austenite phase condition in the deployed configuration.

Lung volume reduction systems, such as those depicted in FIGS. 37-48, comprise an implantable device that is configured to be deliverable into a patient's lung and which is also configured to be reshaped to make the lung tissue that is in contact with the device more curved. Increasing the curvature of the tissue assists in reducing the lung volume of diseased tissue, which in turn increases the lung volume of healthier tissue. In some instances, the devices are configured to be reshaped to a permanent second configuration. However, as will be appreciated by those skilled in the art, the devices can also be adapted and configured to have a first shape and is configured to be strained elastically to a deliverable shape.

As will be appreciated by those skilled in the art, the devices illustrated in FIGS. 37-48 are can be configured to be deliverable into a patient's lung and configured to reshape lung tissue while allowing fluid to flow both directions past the implant.

Figure 49:
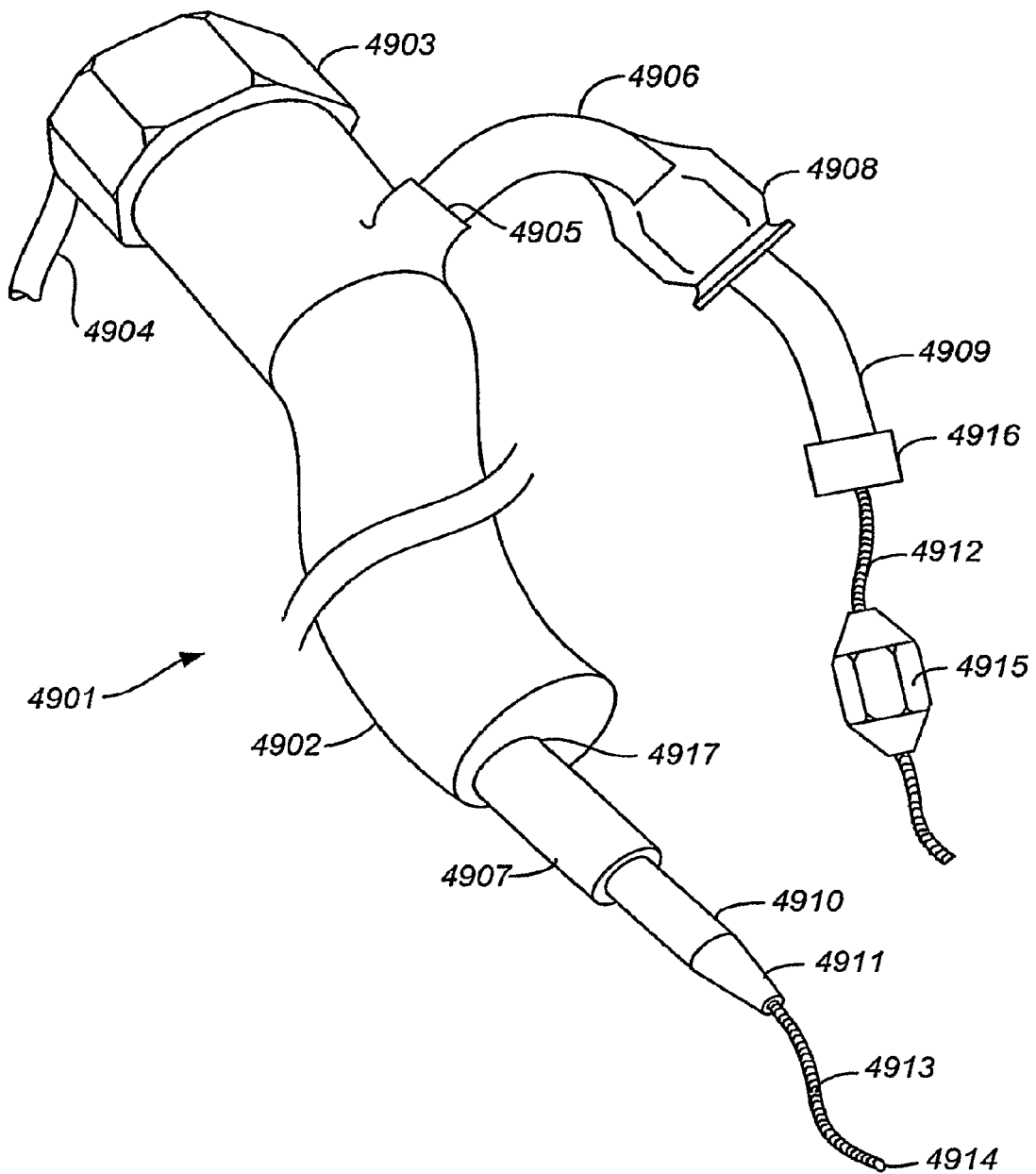
FIG. 49 illustrates a system in an airway with device ready to deliver.

FIG. 49 illustrates a system 4901 that may be used to deliver the implant device. The many components of the system may be needed to guide the bronchoscope 4902 to a site that is appropriate for implant delivery. The airway guide wire has a distal floppy section 4913 that can be steered into any desired airway by rotating the slight curve at the distal tip to the appropriate trajectory at airway bifurcations. To apply torque to the wire, devices such as a locking wire steering handle 4915 may be attached to the proximal end of the wire 4912. The wire tip may be blunt such as the ball tip shown 4914. In some embodiments, the wire may be adapted and configured to pass through a dilator catheter 4909 that is shaped to provide a smooth diameter transition from the wire diameter to the delivery catheter 4906 diameter. The distal tip of the dilator 4910 should be tapered 4911 as shown. The dilator prevents the open end of the delivery catheter 4906 to dig into lung tissue in an unintended way. The dilator hub 4916 may be made as a Y-fitting to allow the user to couple a syringe and inject radiopaque dye through the dilator lumen to increase the visibility of the airways, which facilitates the use of an x-ray guidance system, such as fluoroscopy or computed tomography. The delivery catheter may be used without the wire and dilator. The catheter 4906 is designed to constrain the device in a deliverable shape while it is advanced through the system and into the patient. The distal end 4907 may be configured from a floppier polymer or braid than the proximal end 4906 and the distal tip may further include a radiopaque material associated with the tip, either integral or adjacent, to identify the position of the tip relative to other anatomical locations, such as bones. Providing one or more radiopaque markers facilitates using x-ray guidance system to position the distal end of the device in situ relative to a target anatomy. The proximal termination of the delivery catheter 4908 may further be adapted to incorporate a lockable hub to secure the loading cartridge 3801 with a smooth continuous lumen. The delivery catheter 4906 is shown introduced into the bronchoscope side port 4905 and out the distal end of the scope 4917. A camera 4903 is shown attached to the end of the scope with a cable 4904, or other delivery mechanism, to transmit the image signal to a processor and monitor. The loading cartridge, delivery catheter, dilator, guide wire and wire steering handle may be made from any material identified in this specification or materials well known to be used for similar products used in the human vascular tract by radiologists.

Figure 50:
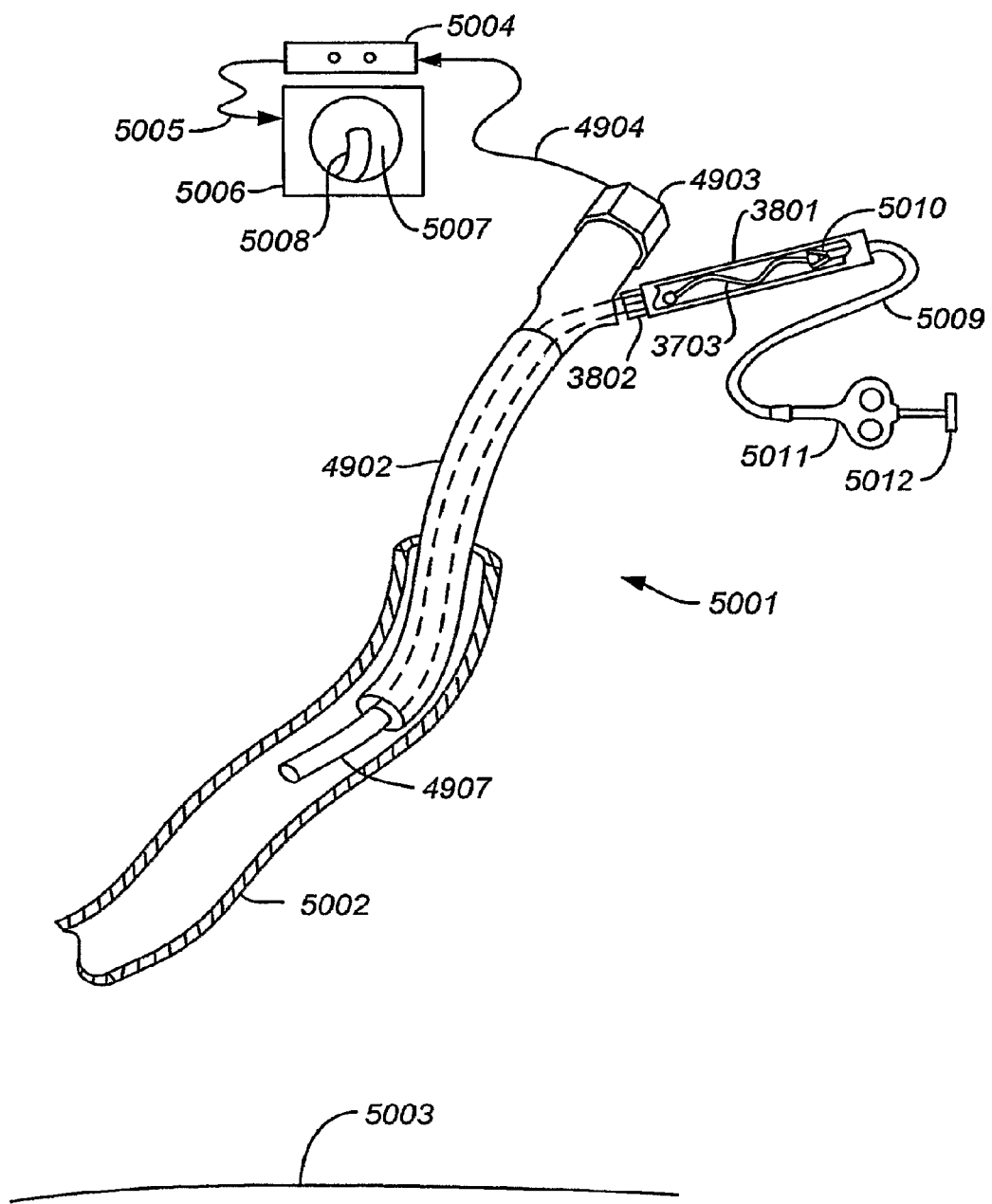
FIG. 50 illustrates a system in an airway delivering the device.

FIG. 50 illustrates a delivery system 5001 that has been placed into a human lung. The bronchoscope 4902 is in an airway 5002. The scope camera 4903 is coupled to a video processor 5004 via a cable 4904. The image is processed and sent through a cable 5005 to a monitor 5006. The monitor shows a typical visual orientation on the screen 5007 of a delivery catheter image 5008 just ahead of the optical element in the scope. The distal end of the delivery catheter 4907 protrudes out of the scope in an airway 5002 where the user will place an implant device 3703. The implant 3703 is loaded into a loading cartridge 3801 that is coupled to the proximal end of the delivery catheter via locking hub connection 3802. A pusher grasper device 5009 is coupled to the proximal end of the implant 3703 with a grasper coupler 5010 that is locked to the implant using an actuation plunger 5012, handle 5011 and pull wire that runs through the central lumen in the pusher catheter. By releasably coupling the pusher to the implant device, the user may advance the implant to a position in the lung in a deployed configuration. The user can survey the implant placement position and still be able to retrieve the implant back into the delivery catheter, with ease, if the delivery position is less than ideal. The device has not been delivered and the bottom surface of the lung 5003 is shown as generally flat and the airway is shown as generally straight. These are both anatomically correct for a lung with no implant devices. If the delivery position is correct, the user may actuate the plunger 5012 to release the implant into the patient.

Figure 51:
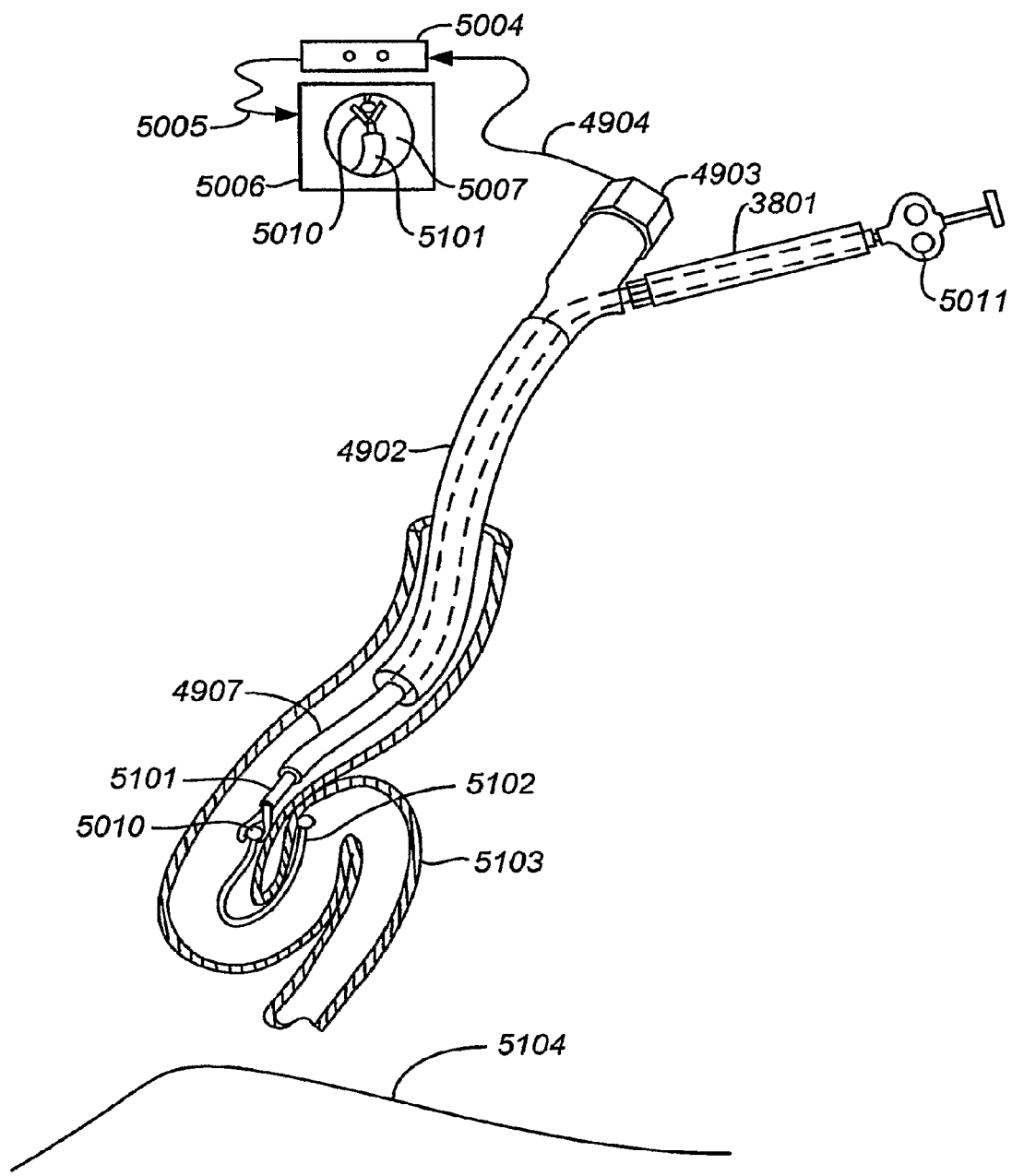
FIG. 51 illustrates a system in an airway with the device delivered.

FIG. 51 illustrates generally the same system after the implant has been deployed into the airway 5103. The implant 5102 and pusher 5101 has been advanced through the delivery catheter 4907 to a location distal to the scope 4902. The pusher grasping jaws 5010 are still locked onto the proximal end of the implant 5102 but the implant has recovered to a pre-programmed shape that has also bent the airway 5103 into a folded configuration. By folding the airway, the airway structure has been effectively shortened within the lung.

Since the airways are well anchored into the lung tissue, the airway provides tension on the surrounding lung tissue which is graphically depicted by showing the pulled (curved inward) floor of the lung 5104. The image from the camera 4903 is transmitted through the signal processor 5004 to the monitor 5006 to show the distal tip of the delivery catheter 5101, distal grasper of the pusher 5010 and proximal end of the implant 3703. The grasper may be used to locate, couple to and retrieve devices that have been released in the patient. It is easy to envision how the implant performs work on the airways and lung tissue without blocking the entire lumen of the airway. This is a benefit in that fluid or air may pass either way through the airway past the implant device.

As will be appreciated by those skilled in the art, the device can be manufactured and deployed such that it is deliverable through a bronchoscope. When actuated, the device can be adapted and configured to bend or curl which then distorts lung tissue with which the device comes in contact. Lung tissues that may be beneficially distorted by the device are airways, blood vessels, faces of tissue that have been dissected for introduction of the device or a combination of any of these. By compressing the lung tissue, the device can result in an increase in elastic recoil and tension in the lung in at least some cases. Additionally, in some instances, lung function can be at least partially restored regardless of the amount of collateral ventilation. Further, the diaphragm may, in some instances, move up once greater tension is created which enables the lung cavity to operate more effectively.

Devices according to the invention have a small cross-section, typically less than 10 F. The flexibility of the device prior to deployment facilitates advancement of the device through the tortuous lung anatomy. Once deployed, the device can remain rigid to hold and maintain a tissue deforming effect. Further, the device design facilitates recapture, de-activation and removal as well as adjustment in place.

Candidate materials for the devices and components described herein would be known by persons skilled in the art and include, for example, suitable biocompatible materials such as metals (e.g. stainless steel, shape memory alloys, such a nickel titanium alloy (nitinol), titanium, and cobalt) and engineering plastics (e.g. polycarbonate). See, for example U.S. Pat. Nos. 5,190,546 to Jervis for Medical Devices Incorporating SIM Memory Alloy Elements, and 5,964,770 to Flomenblit for High Strength Medical Devices of Shape Memory Alloy. In some embodiments, other materials may be appropriate for some or all of the components, such as biocompatible polymers, including polyetheretherketone (PEEK), polyarylamide, polyethylene, and polysulphone.

Polymers and metals used to make the implant and delivery system should be coated with materials to prevent the formation and growth of granular tissue, scar tissue and mucus. Many of the drugs used with stent products to arrest hyperplasia of smooth muscle cells in blood vessels after deploying metallic stents will work very well for these devices. Slow release drug eluting polymers or solvents may be used to regulate the release of drugs that include any substance capable of exerting a therapeutic or prophylactic effect for a patient. For example, the drug could be designed to inhibit the activity of smooth muscle cells. It can be directed at inhibiting abnormal or inappropriate migration and/or proliferation of smooth muscle cells to inhibit tissue mass buildup. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin I], actinomycin Xi, and actinomycin C\. The active agent can also fall under the genus of antineoplastic, anti-inflammatory, antiplatelet, anticoagulant, antif[iota]brin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn of Peapack N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hh/IIIa platelet membrane receptor antagonist antibody, recombinant hirudin, and thrombin inhibitors such as Angiomax™ (Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or Hsinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument. Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 A1, to Victrex Manufacturing Ltd. entitled Bio-Compatible Polymeric Materials; PCT Publication WO 02/00275 A1, to Victrex Manufacturing Ltd. entitled Bio-Compatible Polymeric Materials; and PCT Publication WO 02/00270 A1, to Victrex Manufacturing Ltd. entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

The implant described herein can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims presented will define the scope of the invention and that methods and structures within the scope of these claims and their equivalents be covered thereby.

What is claimed is:

1. A system for treating a patient having a lung with an airway, the airway having an airway path prior to treatment, the system comprising:
   a bronchoscope having an elongate bronchoscope insertion tube, the insertion tube extending from a proximal working head to a distal end with a working channel therebetween, the distal end of the insertion tube configured to be inserted distally into an airway and having a scope oriented distally so as to acquire an image from within the airway distally of the distal end of the insertion tube;
   an airway delivery catheter having a proximal end and a distal end with a delivery lumen therebetween, the delivery catheter receivable within the working channel of the bronchoscope, the distal end of the delivery catheter configured for advancement distally of the distal end of the insertion tube along the path of the airway; and
   an implant including an elongate body extending between a proximal end and a distal end, the elongate body having a relatively straight configuration and a bent configuration, the elongate body in the straight configuration extending along an axis and advanceable within the delivery lumen into the airway so as to extend along the path of the airway, the elongate body of the implant configured to deploy from the straight configuration to the bent configuration within the airway so as to move the elongate body adjacent the distal end laterally from the axis and impart bending force on the airway such that the path of the airway bends.

2. The system of claim 1, wherein the implant comprises an elongate implantable spring element having the straight configuration and the axially bent configuration, the elongate spring element in the straight configuration extending along the axis sufficiently for axial insertion into the airway of the lung, an end of the elongate spring element moving laterally from the axis so as to impart the bending force on the lung tissue when released within the airway, the bending force being sufficient to laterally bend the airway.

3. An implant for use in a system and for treating a patient, the patient having a lung with an airway, the airway having an airway path prior to treatment, the system including a bronchoscope having a working channel and a distally oriented viewing scope, the system also including a delivery catheter having a delivery lumen and advanceable from the working channel of the bronchoscope along the path of the airway, the implant comprising:
   an elongate implantable spring element having a proximal end and a distal end, the spring element configured to be constrained into a relatively straight shape by the delivery catheter when disposed in the delivery lumen so as to extend along an axis, the spring element in the straight shape configured for advancement axially from the bronchoscope for delivery to the lung airway so as to extend axially along the path of the airway, the spring element biased to bend the spring element adjacent the distal end away from the axis when disposed in the airway unconstrained by the delivery catheter so as to impart bending force on the airway to cause the airway to be bent from the path.

4. The implant of claim 3 wherein the implant is made, at least partially, of spring material that will fully recover after having been strained at least 1%.

5. The implant of claim 3 wherein the implant comprises a metal, the metal including Nickel and Titanium.

6. The implant of claim 5 wherein the implant wherein the spring element is temperature activated during deployment.

7. A system for use with a bronchoscope and for treating a patient, the patient having a lung with lung tissue including an airway, the airway having an airway path prior to treatment, the bronchoscope having a working channel and a viewing scope for viewing distally within the airway, the system comprising:
   a lung airway delivery catheter having a proximal end and a distal end with a delivery lumen therebetween, the distal end of the delivery catheter configured to be advanced distally from the working channel of the bronchoscope along the path of the airway;
   an implantable device having an elongate body receivable within the delivery lumen and that is configured to be deployed from the delivery lumen into the airway of the lung of the patient, the elongate body configured to extend along an axis in a first configuration when disposed within the delivery catheter for axial insertion along the path of the airway, the elongate body of the implantable device configured to be reshaped from the first configuration to a second configuration within the airway, the elongate body in the second configuration configured to bend laterally away from the axis so as bend the path of the airway.

8. The system of claim 7 wherein the device is reshaped by releasing the device from the delivery catheter, wherein the device has first and second ends separated by a first length when in the first configuration, the first end being blunt so as to inhibit penetration of the lung airway, and wherein the elongate body is configured such that reshaping of the device within the airway bends the airway so that the airway between the ends curves laterally away from between the ends, so that the distance between the ends is less than the first length, and so that lung tissue adjacent the airway and between the ends of the deployed device is compressed.

9. The system of claim 7 wherein the device is configured to be reshaped to a permanent second configuration.

10. The system of claim 7 wherein the device has a first shape and is configured to be strained elastically to a deliverable shape of the first configuration.

11. The system of claim 7 wherein the implant has a first shape and is adapted to be elastically constrained by the delivery catheter to the first configuration whereby removal of the delivery catheter allows the implant to recoil and be reshaped closer to its first shape.

12. The system of claim 11, further comprising a plurality of implants, each implant being configured to be delivered to and reshaped within an associated airway region so as to reduce lung volume.

13. The system of claim 12 wherein the implants are configured to be coupled to other implants when deployed.

14. The system of claim 7 wherein the implant in the second configuration is shorter in length than the implant in the first configuration.

15. The system of claim 7 wherein the distance between the two ends of the implant is reduced when the implant is reshaped.

16. The system of claim 7 wherein the implant is configured to reduce lung volume when the implant occupies less than the entire lumen cross sectional area of a lung airway.

17. The system of claim 7 wherein the implant in the first configuration fits within a cylindrical space that is 18 mm in diameter or smaller.

18. The system of claim 7 wherein a surface area of the implant that is oriented for contact with tissue of the lung is larger than 1.0E-6 square inches per linear inch of length of the implant.

19. The lung volume reduction system of claim 7, wherein the elongate body has an axial length, wherein the elongate body is configured so that reshaping of the implant moves a bearing area extending along the length of the elongate body against the airway sufficiently to bend the airway.

20. The system of claim 7 wherein the implant is coated with material that reduces the rate of wound healing, tissue remodeling, inflammation, generation of granular tissue or a combination of these.

21. The system of claim 7 wherein the reshaped implant is configured to lie within a single plane.

22. The system of claim 7 wherein the reshaped implant is configured to not lie within a single plane.

23. The system of claim 22 wherein the reshaped implant is generally in the shape of a baseball seam or a coil.

24. The system of claim 23 wherein the reshaped implant is generally in the shape of a C or an S.

25. The system of claim 7 wherein the implantable device is made of a resiliently bendable material.

26. The system of claim 7 wherein the system further comprises an actuator adapted to be operated from outside the patient to reshape the implant.

27. The system of claim 7 wherein the system further comprises a pusher adapted to deliver the implant from the catheter into the patient's lung.

28. The system of claim 27 wherein the pusher is releaseably coupled to the implant device so as to allow the implant to be retrieved into the delivery lumen of the catheter so as to allow retrieval of the implant after the implant has been pushed out of the delivery lumen and into the airway.

29. The system of claim 7 wherein the system further comprises a recapture device to remove the implant from a patient's lung.

30. The system of claim 29 wherein the recapture device can be coupled to the proximal end of the implant and is configured to operate within the retrieval catheter or bronchoscope working channel.

31. The system of claim 7 wherein the system further comprises:
a resilient wire receivable within the delivery catheter, wherein the resilient wire is configured to guide the catheter distally of the bronchoscope within the airway.

32. The system of claim 7 wherein an arc length of the implant remains constant as the implant is reshaped.

33. The system of claim 7 wherein the implant further comprising rounded structures at the proximal end and at the distal end of the elongate body so as to inhibit trauma to the airway at the distal and proximal ends of the implant.

34. The system of claim 7 wherein the implant comprises a central wire that spans the length of the implant.

35. The system of claim 34 wherein the central wire is wrapped by a wire frame or covering that is configured to contact lung tissue.

36. A device for use in a system and for treating a patient having a lung with an airway lumen, the airway lumen having an airway path prior to treatment, the system including a bronchoscope having a working channel and a scope for viewing within the airway, the device comprising:
an elongate body having a proximal end and a distal end, the elongate body having a delivery configuration and a deployed configuration, the elongate body in the delivery configuration extending relatively straight along an axis and being adapted to be inserted within the working channel of the bronchoscope and advanced into the airway a lumen adjacent a region of lung tissue targeted for compression so as to extend along the airway path, the device configured for deployment from the delivery configuration to the deployed configuration within the airway lumen, the deployed configuration being more curved than the delivery configuration so that the elongate body, after deployment, bends the airway lumen away from the axis between the proximal and distal ends and locally compresses the region of lung tissue.

37. The device of claim 36, wherein the device is configured to reshape the region of lung tissue while allowing fluid to flow along the airway lumen in both directions past the device.

38. The device of claim 36, wherein the device is configured to be reshaped to a shape that is not axi-symmetric to bend the region of lung tissue.

* * * * *

UNITED STATES PATENT AND TRADEMARK OFFICE
CERTIFICATE OF CORRECTION

| | | |
|---|---|---|
| PATENT NO. | : 8,282,660 B2 | Page 1 of 1 |
| APPLICATION NO. | : 12/167167 | |
| DATED | : October 9, 2012 | |
| INVENTOR(S) | : David Thompson et al. | |

It is certified that error appears in the above-identified patent and that said Letters Patent is hereby corrected as shown below:

On the title page item (63):
'Continuation of application No. PCT/US2007/006339, filed on Mar. 13, 2007, which is a continuation-in-part of application No. 11/422,047, filed on Jun. 2, 2006, now Pat. No. 8,157,537.'

Should read as follows:
'Continuation of application No. PCT/US2007/006339, filed on Mar. 13, 2007, which is a continuation-in-part of application No. 11/422,047, filed on Jun. 2, 2006, now Pat. No. 8,157,837.'

Signed and Sealed this
Ninth Day of September, 2014

Michelle K. Lee
*Deputy Director of the United States Patent and Trademark Office*